(12) United States Patent
Capelli et al.

(10) Patent No.: US 12,138,487 B2
(45) Date of Patent: Nov. 12, 2024

(54) PULSED ACOUSTIC WAVE DERMAL CLEARING SYSTEM AND METHOD

(71) Applicant: Soliton, Inc., Houston, TX (US)

(72) Inventors: Christopher Capelli, Houston, TX (US); David Robertson, Houston, TX (US)

(73) Assignee: Soliton, Inc., Houston, TX (US)

( * ) Notice: Subject to any disclaimer, the term of this patent is extended or adjusted under 35 U.S.C. 154(b) by 1111 days.

(21) Appl. No.: 16/087,976

(22) PCT Filed: Mar. 23, 2017

(86) PCT No.: PCT/US2017/023728
§ 371 (c)(1),
(2) Date: Sep. 24, 2018

(87) PCT Pub. No.: WO2017/165595
PCT Pub. Date: Sep. 28, 2017

(65) Prior Publication Data
US 2020/0206072 A1 Jul. 2, 2020

Related U.S. Application Data

(60) Provisional application No. 62/312,372, filed on Mar. 23, 2016.

(51) Int. Cl.
*A61H 23/00* (2006.01)
*A61B 17/00* (2006.01)
(Continued)

(52) U.S. Cl.
CPC .............. *A61N 7/00* (2013.01); *A61B 18/203* (2013.01); *A61B 2017/00769* (2013.01);
(Continued)

(58) Field of Classification Search
CPC .. A61H 23/008; A61H 23/0245; A61H 23/04; A61H 2201/10; A61H 2201/1207;
(Continued)

(56) References Cited

U.S. PATENT DOCUMENTS

| | | | |
|---|---|---|---|
| 3,234,429 | A | 2/1966 | Schrom |
| 3,364,708 | A | 1/1968 | Padberg |

(Continued)

FOREIGN PATENT DOCUMENTS

| | | |
|---|---|---|
| CN | 1245410 | 2/2000 |
| CN | 101028525 | 9/2007 |

(Continued)

OTHER PUBLICATIONS

Boxman, et al., "Handbook of Vacuum Arc Science and Technology: Fundamentals and Applications," Park Ridge, New Jersey: Noyes Publications, pp. 316-319, 1995.

(Continued)

*Primary Examiner* — Lynsey C Eiseman
*Assistant Examiner* — Daniel Tehrani
(74) *Attorney, Agent, or Firm* — Mintz, Levin, Cohn, Ferris, Glovsky and Popeo, P.C.

(57) ABSTRACT

Methods and systems for method for acoustic treatment of tissue to disperse vacuoles within the tissue. Some of the present methods and systems comprise: directing pulsed acoustic waves from the acoustic wave generator into the tissue containing the vacuoles. Some of the present methods include identifying the location of tissue containing vacuoles, and/or coupling (e.g., acoustically) an acoustic wave generator to the tissue containing the vacuoles.

12 Claims, 21 Drawing Sheets

(51) Int. Cl.
   *A61B 17/22*   (2006.01)
   *A61B 18/00*   (2006.01)
   *A61B 18/20*   (2006.01)
   *A61H 23/02*   (2006.01)
   *A61H 23/04*   (2006.01)
   *A61N 7/00*    (2006.01)

(52) U.S. Cl.
   CPC ............... *A61B 2018/00458* (2013.01); *A61B 2018/0047* (2013.01); *A61B 2018/00476* (2013.01); *A61N 2007/0034* (2013.01)

(58) Field of Classification Search
   CPC .. A61B 2018/00458; A61B 2018/0047; A61B 2018/00476; A61B 18/203; A61B 17/22004; A61B 2017/00769
   See application file for complete search history.

(56) References Cited

U.S. PATENT DOCUMENTS

| | | |
|---|---|---|
| 3,475,646 A | 10/1969 | Chapman |
| 3,604,641 A | 9/1971 | Wilson et al. |
| 3,613,069 A | 10/1971 | Cary |
| 3,735,764 A | 5/1973 | Balev |
| 3,769,963 A | 11/1973 | Goldman |
| 3,942,531 A | 3/1976 | Hoff |
| 3,983,749 A | 10/1976 | Fletcher et al. |
| 4,005,314 A | 1/1977 | Zinn |
| 4,311,147 A | 1/1982 | Hausler |
| 4,556,051 A | 12/1985 | Maurer |
| 4,608,979 A | 9/1986 | Breidenthal et al. |
| 4,715,376 A | 12/1987 | Nowacki et al. |
| 4,858,597 A | 8/1989 | Kurtze et al. |
| 4,868,791 A | 9/1989 | Cathignol et al. |
| 4,896,673 A | 1/1990 | Rose et al. |
| 4,905,671 A | 3/1990 | Senge et al. |
| 4,928,671 A | 5/1990 | Reichenberger et al. |
| 4,955,143 A | 9/1990 | Hagelauer |
| 4,962,752 A | 10/1990 | Reichenberger et al. |
| 4,979,501 A | 12/1990 | Valchanov et al. |
| 5,009,232 A | 4/1991 | Hassler et al. |
| 5,015,929 A | 5/1991 | Cathignol et al. |
| 5,071,422 A | 12/1991 | Watson et al. |
| 5,146,912 A | 9/1992 | Eizenhoefer |
| 5,149,406 A | 9/1992 | Mullen et al. |
| 5,150,713 A | 9/1992 | Okazaki |
| 5,193,527 A | 3/1993 | Schafer |
| 5,195,508 A | 3/1993 | Muller et al. |
| 5,204,820 A | 4/1993 | Strobel et al. |
| 5,231,976 A | 8/1993 | Wiksell |
| 5,240,005 A | 8/1993 | Viebach |
| 5,245,988 A | 9/1993 | Einars et al. |
| 5,259,368 A | 11/1993 | Wiksell |
| 5,269,292 A | 12/1993 | Granz et al. |
| 5,284,143 A | 2/1994 | Rattner |
| 5,304,170 A | 4/1994 | Green |
| 5,304,207 A | 4/1994 | Stromer |
| 5,327,890 A | 7/1994 | Matura et al. |
| 5,360,447 A | 11/1994 | Koop |
| 5,374,236 A | 12/1994 | Hassler |
| 5,393,296 A | 2/1995 | Rattner |
| 5,409,446 A | 4/1995 | Rattner |
| 5,419,327 A | 5/1995 | Rohwedder et al. |
| 5,423,803 A | 6/1995 | Tankovich et al. |
| 5,435,304 A | 7/1995 | Oppelt et al. |
| 5,458,652 A | 10/1995 | Uebelacker |
| 5,509,200 A | 4/1996 | Frankeny et al. |
| 5,529,572 A | 6/1996 | Spector |
| 5,595,178 A | 1/1997 | Voss et al. |
| 5,618,275 A | 4/1997 | Bock |
| 5,658,239 A | 8/1997 | Delmenico |
| 5,675,495 A | 10/1997 | Biermann et al. |
| 5,676,159 A | 10/1997 | Navis |
| 5,709,676 A | 1/1998 | Alt |
| 5,722,411 A | 3/1998 | Suzuki |
| 5,737,462 A | 4/1998 | Whitehouse et al. |
| 5,790,305 A | 8/1998 | Marcellin-Dibon et al. |
| 5,827,204 A | 10/1998 | Grandia et al. |
| 5,879,314 A | 3/1999 | Peterson et al. |
| 6,013,122 A | 1/2000 | Klitzman et al. |
| 6,036,661 A | 3/2000 | Schwarze et al. |
| 6,039,694 A | 3/2000 | Larson |
| 6,058,932 A | 5/2000 | Hughes |
| 6,080,119 A | 6/2000 | Schwarze et al. |
| 6,096,029 A | 8/2000 | O'Donnell, Jr. |
| 6,113,559 A | 9/2000 | Klopotek |
| 6,113,560 A | 9/2000 | Simnacher |
| 6,123,679 A | 9/2000 | Lafaut et al. |
| 6,176,839 B1 | 1/2001 | Deluis et al. |
| 6,186,963 B1 | 2/2001 | Schwarze et al. |
| 6,210,329 B1 | 4/2001 | Christmas |
| 6,217,531 B1 | 4/2001 | Reitmajer |
| 6,309,355 B1 | 10/2001 | Cain et al. |
| 6,325,769 B1 | 12/2001 | Klopotek |
| 6,350,245 B1 | 2/2002 | Cimino |
| 6,368,929 B1 | 4/2002 | Hill et al. |
| 6,390,995 B1 | 5/2002 | Ogden et al. |
| 6,450,979 B1 | 9/2002 | Miwa et al. |
| 6,454,713 B1 | 9/2002 | Ishibashi et al. |
| 6,487,447 B1 | 11/2002 | Weimann et al. |
| 6,491,685 B2 | 12/2002 | Visuri |
| 6,500,141 B1 | 12/2002 | Irion et al. |
| 6,515,842 B1 | 2/2003 | Hayworth et al. |
| 6,519,376 B2 | 2/2003 | Biagi et al. |
| 6,551,308 B1 | 4/2003 | Muller et al. |
| 6,666,834 B2 | 12/2003 | Restle et al. |
| 6,755,821 B1 | 6/2004 | Fry |
| 6,800,122 B2 | 10/2004 | Anderson et al. |
| 6,905,467 B2 | 6/2005 | Bradley |
| 6,942,663 B2 | 9/2005 | Vargas et al. |
| 6,948,843 B2 | 9/2005 | Laugharn et al. |
| 6,972,116 B2 | 12/2005 | Brill et al. |
| 7,189,209 B1 | 3/2007 | Ogden et al. |
| 7,250,047 B2 | 7/2007 | Anderson et al. |
| 7,258,674 B2 | 8/2007 | Cribbs et al. |
| 7,311,678 B2 | 12/2007 | Spector |
| 7,347,855 B2 | 3/2008 | Eshel et al. |
| 7,364,554 B2 | 4/2008 | Bolze et al. |
| 7,405,510 B2 | 6/2008 | Kaminski et al. |
| 7,470,240 B2 | 12/2008 | Schultheiss et al. |
| 7,507,213 B2 | 3/2009 | Schultheiss et al. |
| 7,544,171 B2 | 6/2009 | Schaden et al. |
| 7,588,547 B2 | 9/2009 | Deem et al. |
| 7,867,178 B2 | 1/2011 | Simnacher |
| 7,985,189 B1 | 7/2011 | Ogden et al. |
| 7,988,631 B2 | 8/2011 | Bohris |
| 8,057,408 B2 | 11/2011 | Cain et al. |
| 8,088,073 B2 | 1/2012 | Simnacher et al. |
| 8,092,401 B2 | 1/2012 | Schultheiss |
| 8,102,734 B2 | 1/2012 | Sliwa et al. |
| 8,235,899 B2 | 8/2012 | Hashiba |
| 8,257,282 B2 | 9/2012 | Uebelacker et al. |
| 8,298,162 B2 | 10/2012 | Del Giglio |
| 8,323,220 B2 | 12/2012 | Babaev |
| 8,343,420 B2 | 1/2013 | Cioanta et al. |
| 8,357,095 B2 | 1/2013 | Anderson et al. |
| 8,672,721 B2 | 3/2014 | Camilli |
| 8,684,970 B1 | 4/2014 | Koyfman |
| 8,840,608 B2 | 9/2014 | Anderson et al. |
| 2002/0009015 A1 | 1/2002 | Laugharn et al. |
| 2002/0193831 A1 | 12/2002 | Smith |
| 2003/0167964 A1 | 9/2003 | Anderson et al. |
| 2003/0176873 A1 | 9/2003 | Chernenko et al. |
| 2003/0233045 A1 | 12/2003 | Vaezy |
| 2004/0006288 A1 | 1/2004 | Spector et al. |
| 2004/0181219 A1 | 9/2004 | Goble et al. |
| 2005/0015023 A1 | 1/2005 | Ein-Gal |
| 2005/0049543 A1 | 3/2005 | Anderson et al. |
| 2005/0107852 A1 | 5/2005 | Levernier et al. |
| 2005/0137656 A1 | 6/2005 | Malak |
| 2005/0150830 A1 | 7/2005 | Laugharn |
| 2006/0036168 A1 | 2/2006 | Liang et al. |
| 2006/0064082 A1 | 3/2006 | Bonutti |

(56) References Cited

U.S. PATENT DOCUMENTS

| | | |
|---|---|---|
| 2006/0094988 A1 | 5/2006 | Tosaya et al. |
| 2006/0158956 A1 | 7/2006 | Laugharn et al. |
| 2006/0173388 A1 | 8/2006 | Ginter et al. |
| 2006/0184071 A1 | 8/2006 | Klopotek |
| 2006/0200116 A1 | 9/2006 | Ferren et al. |
| 2006/0211958 A1 | 9/2006 | Rosenberg et al. |
| 2007/0016112 A1 | 1/2007 | Schultheiss et al. |
| 2007/0038060 A1 | 2/2007 | Cerwin et al. |
| 2007/0049829 A1 | 3/2007 | Kaminski et al. |
| 2007/0055157 A1 | 3/2007 | Bohris |
| 2007/0055180 A1 | 3/2007 | Deem et al. |
| 2007/0065420 A1 | 3/2007 | Johnson |
| 2007/0135755 A1 | 6/2007 | Bernabei et al. |
| 2007/0198068 A1* | 8/2007 | Chan .................... A61B 18/203 607/88 |
| 2007/0219760 A1 | 9/2007 | Yang et al. |
| 2007/0239072 A1 | 10/2007 | Schultheiss |
| 2007/0239082 A1 | 10/2007 | Schultheiss et al. |
| 2007/0239084 A1 | 10/2007 | Voss |
| 2007/0249939 A1 | 10/2007 | Gerbi et al. |
| 2008/0009774 A1 | 1/2008 | Capelli et al. |
| 2008/0009885 A1 | 1/2008 | Del Giglio |
| 2008/0021447 A1 | 1/2008 | Davison et al. |
| 2008/0071198 A1 | 3/2008 | Ogden et al. |
| 2008/0107744 A1 | 5/2008 | Chu |
| 2008/0132810 A1 | 6/2008 | Scoseria et al. |
| 2008/0146971 A1 | 6/2008 | Uebelacker et al. |
| 2008/0154157 A1 | 6/2008 | Altshuler et al. |
| 2008/0183200 A1 | 7/2008 | Babaev |
| 2008/0194967 A1 | 8/2008 | Sliwa et al. |
| 2008/0195003 A1 | 8/2008 | Sliwa et al. |
| 2008/0262483 A1* | 10/2008 | Capelli .................... A61N 7/02 601/4 |
| 2008/0269163 A1 | 10/2008 | Sostaric |
| 2008/0269608 A1 | 10/2008 | Anderson et al. |
| 2008/0319356 A1 | 12/2008 | Cain et al. |
| 2009/0018472 A1 | 1/2009 | Soltani et al. |
| 2009/0062644 A1 | 3/2009 | McMorrow et al. |
| 2009/0275832 A1 | 11/2009 | Gelbart |
| 2010/0049098 A1 | 2/2010 | Shalgi et al. |
| 2010/0076349 A1 | 3/2010 | Babaev |
| 2010/0082019 A1 | 4/2010 | Neev |
| 2010/0087899 A1 | 4/2010 | Erez et al. |
| 2010/0168575 A1 | 7/2010 | Hashiba |
| 2010/0204617 A1 | 8/2010 | Ben-Ezra |
| 2010/0208467 A1 | 8/2010 | Dross |
| 2010/0249768 A1 | 9/2010 | Avramenko et al. |
| 2010/0274161 A1 | 10/2010 | Azhari et al. |
| 2010/0280420 A1 | 11/2010 | Barthe et al. |
| 2010/0331741 A9 | 12/2010 | Cioanta et al. |
| 2011/0034832 A1 | 2/2011 | Cioanta et al. |
| 2011/0087157 A1 | 4/2011 | Cioanta et al. |
| 2011/0319793 A1 | 12/2011 | Hynynen |
| 2012/0157892 A1 | 6/2012 | Reitmajer et al. |
| 2012/0167174 A1 | 6/2012 | Saxena et al. |
| 2012/0253240 A1 | 10/2012 | Uebelacker et al. |
| 2012/0253416 A1 | 10/2012 | Erez et al. |
| 2012/0271169 A1 | 10/2012 | Coussios et al. |
| 2012/0310232 A1 | 12/2012 | Erez |
| 2012/0323147 A1 | 12/2012 | Scheirer |
| 2012/0330288 A1 | 12/2012 | Clementi et al. |
| 2013/0018287 A1 | 1/2013 | Capelli |
| 2013/0046179 A1 | 2/2013 | Humayun |
| 2013/0046207 A1 | 2/2013 | Capelli |
| 2013/0165839 A1 | 6/2013 | O'Neil |
| 2013/0190744 A1 | 7/2013 | Avram et al. |
| 2013/0345600 A1 | 12/2013 | Katragadda et al. |
| 2014/0005576 A1 | 1/2014 | Adams |
| 2014/0094718 A1* | 4/2014 | Feldman .............. A61B 18/203 601/2 |
| 2014/0228820 A1 | 8/2014 | Blaskowski et al. |
| 2014/0243715 A1 | 8/2014 | Cioanta et al. |
| 2014/0243847 A1 | 8/2014 | Hakala et al. |
| 2014/0257144 A1* | 9/2014 | Capelli ................ A61B 17/225 601/2 |
| 2014/0276693 A1 | 9/2014 | Altshuler et al. |
| 2014/0276722 A1 | 9/2014 | Parihar et al. |
| 2014/0277219 A1 | 9/2014 | Nanda |
| 2014/0378740 A1 | 12/2014 | Wagner et al. |
| 2015/0105702 A1 | 4/2015 | Wagner et al. |
| 2015/0126913 A1 | 5/2015 | Jurna et al. |
| 2015/0141877 A1 | 5/2015 | Feldman |
| 2015/0217111 A1 | 8/2015 | Stevenson et al. |
| 2016/0016013 A1 | 1/2016 | Capelli et al. |
| 2016/0022601 A1 | 1/2016 | O'Neil |
| 2016/0067139 A1 | 3/2016 | Katragadda et al. |
| 2016/0166837 A1 | 6/2016 | Strommer et al. |
| 2016/0262778 A1 | 9/2016 | Du |
| 2016/0271419 A1 | 9/2016 | Varghese et al. |
| 2017/0202514 A1 | 7/2017 | Nousiainen et al. |
| 2017/0301474 A1 | 10/2017 | Saito |
| 2018/0078774 A1 | 3/2018 | Strommer et al. |
| 2018/0116905 A1 | 5/2018 | Capelli et al. |
| 2018/0221688 A1 | 8/2018 | Cioanta et al. |

FOREIGN PATENT DOCUMENTS

| | | |
|---|---|---|
| CN | 101146574 | 3/2008 |
| CN | 101155614 | 4/2008 |
| CN | 100530868 | 8/2009 |
| CN | 101610736 | 12/2009 |
| CN | 102057422 | 5/2011 |
| CN | 102247661 | 11/2011 |
| CN | 105209117 | 12/2015 |
| CN | 105246419 | 1/2016 |
| DE | 3150430 | 7/1983 |
| DE | 3710371 | 10/1988 |
| DE | 60008898 | 1/2005 |
| DE | 102007046902 | 4/2009 |
| EP | 0008647 | 3/1980 |
| EP | 0243650 | 11/1987 |
| EP | 0322473 | 7/1989 |
| EP | 0326620 | 8/1989 |
| EP | 2964326 | 1/2016 |
| EP | 3626307 | 3/2020 |
| EP | 2531134 B1 | 9/2020 |
| FR | 2605874 | 5/1988 |
| GB | 2303552 | 2/1997 |
| JP | 53-111689 | 9/1978 |
| JP | S61-293447 | 12/1986 |
| JP | 62-192150 | 8/1987 |
| JP | S 63-023775 | 2/1988 |
| JP | S63-111852 A | 5/1988 |
| JP | S63-183050 | 7/1988 |
| JP | H01-97995 A | 4/1989 |
| JP | H05-207593 A | 8/1993 |
| JP | 6-7365 | 1/1994 |
| JP | H06-505648 | 6/1994 |
| JP | H0673654 | 10/1994 |
| JP | 8-140984 | 6/1996 |
| JP | H 08140984 | 6/1996 |
| JP | 8-194079 | 7/1996 |
| JP | 1996-222472 | 8/1996 |
| JP | H0-8224253 | 9/1996 |
| JP | H08-224253 A | 9/1996 |
| JP | 9-103434 | 4/1997 |
| JP | H09103434 | 4/1997 |
| JP | H 10192289 | 7/1998 |
| JP | H 10328192 | 12/1998 |
| JP | 2003-500126 | 1/2003 |
| JP | 2004526507 | 9/2004 |
| JP | 2005514142 | 5/2005 |
| JP | 2007-000218 | 1/2007 |
| JP | 2009506870 | 2/2009 |
| JP | 2009508649 A | 3/2009 |
| JP | 2009-518126 | 4/2009 |
| JP | 2009-527262 | 7/2009 |
| JP | 2009543614 | 12/2009 |
| JP | 2012-516170 | 7/2012 |
| JP | 2013537559 | 10/2013 |
| JP | 2014-507990 | 4/2014 |
| JP | 2014525782 | 10/2014 |
| JP | 2016/523602 | 8/2016 |
| JP | 2017-500078 | 1/2017 |

(56) References Cited

FOREIGN PATENT DOCUMENTS

| | | |
|---|---|---|
| JP | 6173644 | 8/2017 |
| KR | 101886863 | 8/2018 |
| RU | 2121812 C1 | 11/1998 |
| RU | 2151559 C1 | 6/2000 |
| RU | 2600504 C1 | 10/2016 |
| TW | 200604017 | 2/2006 |
| TW | I 292341 | 1/2008 |
| TW | I 350249 | 10/2011 |
| WO | WO 91/10227 | 7/1991 |
| WO | WO 2000/071207 | 11/2000 |
| WO | WO 2002/030256 | 4/2002 |
| WO | WO 2004/080147 | 9/2004 |
| WO | WO 2007/067563 | 6/2007 |
| WO | WO 2007/088546 | 8/2007 |
| WO | WO 2007/146988 | 12/2007 |
| WO | WO 2008/052198 | 5/2008 |
| WO | WO 2008/074005 | 6/2008 |
| WO | WO 2008/137942 | 11/2008 |
| WO | WO-2009/050719 A2 | 4/2009 |
| WO | WO 2010/086301 | 8/2010 |
| WO | WO 2010/122517 | 10/2010 |
| WO | WO 2011/077466 | 6/2011 |
| WO | WO 2011/091020 | 7/2011 |
| WO | WO 2012/107830 | 8/2012 |
| WO | WO 2013/012724 | 1/2013 |
| WO | WO 2014/138582 | 9/2014 |
| WO | WO 2014/191263 | 12/2014 |
| WO | WO 2015/176001 | 11/2015 |
| WO | WO 2017/165595 | 9/2017 |
| WO | WO 2018/136514 | 7/2018 |

OTHER PUBLICATIONS

Extended European Search Report Issued in Corresponding European Patent Application No. 20153807.1, dated Jun. 9, 2020.
International Preliminary Report on Patentability Issued in Corresponding PCT Application No. PCT/US2017/042122, issued Jan. 22, 2019.
International Search Report and Written Opinion Issued in Corresponding PCT Application No. PCT/US2017/042122, mailed Jan. 9, 2018.
International Search Report and Written Opinion Issued in Corresponding PCT Application No. PCT/US14/21746, mailed Sep. 12, 2014.
Office Action Issued in Corresponding Japanese Patent Application No. 2019-012062, dated Jun. 16, 2020.
Partial Supplementary Search Report Issued in Corresponding European Patent Application No. EP18754679.1, dated Jul. 29, 2020.
Schmitz, et al., "Treatment of Chronic Plantar Fasciopathy with Extracorporeal Shock Waves (Review)," *Journal of Orthopaedic Surgery and Research*, 8(1); 31, 2013.
Ushakov, et al., "Impulse Breakdown of Liquids," New York, New York: Springer.
International Search Report and Written Opinion issued in Application No. PCT/US2017/023728, issued Jun. 9, 2017.
International Preliminary Report on Patentability issued in Application No. PCT/US2017/023728, issued Sep. 25, 2018.
Office Action issued in Corresponding Japanese Application No. 2018-550349, Mar. 31, 2021 (English Translation provided).
Baumler et al., Q-Switch Laser and Tattoo Pigments: First Results of the Chemical and Photophysical Analysis of 41 Compounds, Lasers in Surgery and medicine 26:13-21 (2000), pp. 13-21.
Bickle, Abdominal X Rays Made Easy: Calcification, Student BMJ vol. 10, Aug. 2002, 272-274.
Burov, et al., "Nonlinear Ultrasound: Breakdown of Microscopic Biological Structures and Nonthermal Impact on Malignant Tumor," *Doklady Biochemistry and Biophysics*, 383(3), pp. 101-104. (2002).
Chen et al., "The disappearance of ultrasound contrast bubbles: Observations of bubble dissolution and Cavitation nucleation", Ultrasound in Med. & Biol., vol. 28, No. 6, pp. 793-803, 2002.
Delius, et al., "Biological Effects of Shock Waves: Kidney Haemorrhage by Shock Waves in Dogs—Administration Rate Dependence," *Ultrasound Med Biol.*, 14(8), 689-694, 1988.
Eisenmenger, W. et al., "The First Clinical Results of Wide-Focus and Low-Pressure ESWL" Ultrasound in Med. & Biol., vol. 28, No. 6, pp. 769-774, 2002.
Eisenmenger, Wolfgang, "The Mechanisms of Stone Fragmentation in ESWL", Ultrasound in Med. & Biol., vol. 27, No. 5, pp. 683-693, 2001.
Extended European Search Report Issued in Corresponding European Patent Application No. 17771118.1, dated Oct. 22, 2019.
Falco, "Single-Point Nonlinearity Indicators for the Propagation of High Amplitude Acoustic Signals," Ph.D. Thesis. Graduate Program in Acoustics, The Pennsylvania State University, University Park, PA, May 2007.
Fernando, "A Nonlinear Computational Method for the Propagation of Shock Waves in Aero-Engine Inlets Towards A New Model for Buzz-Saw Noise Prediction," $15^{th}$ AIAA/CEAS Aerocoustics Conference (30th Aerocoustics Conference) May 11-13, 2009, 1-18.
Gillitzer, et al., "Low-Frequency Extracorporeal Shock Wave Lithotripsy Improves Renal Pelvic Stone Disintegration an a Pig Model," *BJU Int*, 176, 1284-1288, 2009.
Ho et al., "Laser-Tattoo Removal—A Study of the Mechanism and the Optimal Treatment Strategy via Computer Simulations", Lasers in Surgery and medicine 30:389-391 (2002).
Kuhn et al., "Impact of extracorporeal shock waves on the human skin with cellulite: A case study of an unique instance", *Clinical Interventions of Aging*, 3(1):201-210, 2008.
Kuperman-Beade et al., "Laser Removal of Tattoos", Am J Clin Dermatol 2001: 2(1):21-25.
Kuzmin et al., "Ultrasonic Cavitational Chemical Technologies", XI Session of the Russian Acoustical Society, Moscow, Nov. 19-23, 2001.
Liu, et al., "Optimized Design of LED Freeform Lens For Uniform Circular Illumination," *Journal of Zhejiang University-Science C*, Computer & Electron, 13(12), 929-936, 2012.
Madbouly, et al., "Slow Versus Fast Shock Wave Lithotripsy Rate for Urolithiasis: A Prospective Randomized Study," *The Journal of Urology*, 173, 127-130, 2005.
Nana, et al., "Application of the Multiple Low-Energy Q-Switched Laser for the Treatment of Tattoos in 21 Cases," China Aesthetic Medicine, 4(21), 621-622, 2012. (English Abstract).
Ng et al., "Therapeutic Ultrasound: Its Application in Drug Delivery", Medicinal Research Reviews, vol. 22, No. 2, 204-223, 2002.
Office Action issued in Corresponding Chinese Patent Application No. 201780030448, dated Apr. 15, 2020.
Ogden et al., Principles of Shock Wave Therapy, Clinical Orthopaedics and Related Research, No. 387, pp. 8-17, 2001.
Reichenberger, "Electromagnetic Acoustic Source for Extracorporeal Generation of Shock Waves in Lithotripsy," Siemens Forsch, 1986, 187-194.
Ross et al., "Comparison of Responses of Tattoos to Picosecond and Nanosecond Q-Switched Neodymium: YAG Lasers" ARCH Dermatol/vol. 134, Feb. 1998, pp. 167-171.
Sheth and Pandya, "Melsama: A comprehensive update (Part I)", *Journal of the American Academy of Dermatology*, 65:689-697, 2011.
Sheth and Pandya, "Melsama: A comprehensive update (Part II)", *Journal of the American Academy of Dermatology*, 65:699-714, 2011.
Solis et al., "Experimental Nonsurgical Tattoo Removal in a Guinea Pig Model with Topical Imiquimod and Tretinoin", Dermatol Surg. 2002, 28:83-87.
Timko et al., "In Vitro Quantitative Chemical Analysis of Tattoo Pigments", ARCH Dermatol/vol. 137, Feb. 2001, pp. 143-147.
Varma, S., "Tattoo Ink Darkening of a yellow Tattoo after Q-Switched Laser Treatment", 2002 Blackwell Science Ltd., Clinical and Experimental Dermatology, 27, 461-463.
Vogel, et al., "Shock Wave Emission and Cavitation Bubble Generation by Picosecond and Nanosecond Optical Breakdown in Water," J. Acoust. Soc Am. 100(1), Jul. 1996.

(56) References Cited

OTHER PUBLICATIONS

Wolfrum et al., "Shock wave induced interaction of microbubbles and boundaries", Physics of Fluids, vol. 15, No. 10, Oct. 2003, pp. 2916-2922.
Official Action issued in Japanese Patent Application No. 2019-544631, dated Sep. 16, 2022.
Official Action issued in U.S. Appl. No. 13/547,995, dated Sep. 15, 2022.
Official Action issued in U.S. Appl. No. 16/319,509, dated Sep. 20, 2022.
Official Action issued in U.S. Appl. No. 16/486,920, dated Sep. 14, 2022.
International Search Report and Written Opinion issued in Corresponding PCT Application No. PCT/US2020/026425, dated Sep. 2, 2020.
Office Action and Search Report issued in Corresponding Chinese Application No. 201780056472.0, dated Jan. 19, 2022 (English Translation provided).
Office Action issued in Australian Patent Application No. 2021201670, dated Jun. 20, 2022.
Office Action issued in U.S. Appl. No. 16/478,611, dated Jun. 30, 2022.
Troilius, "Effective Treatment of traumatic Tattoos with a Q-switched Nd:YAG laser," Lasers Surg. Med., 22:103-108, 1998.
Carlberg, "Upgrading from Stepper to Servo," Yaskawa America Inc., pp. 1-7, 2011.
Manousakas et al., "Development of a system of automatic gap-adjusted electrodes for shock wave generators," Review of Scientific Instruments, 75(11):4811-4819, 2004.
Office Action issued in U.S. Appl. No. 16/478,611, dated Oct. 31, 2022.
English translation of Office Action issued in Korean Patent Application No. 10-2019-7005043 dated Sep. 28, 2022.
English translation of Office Action issued in Japanese Patent Application No. 2021- 184610, dated Nov. 18, 2022.
Office Action issued in Australian Patent Application No. 2018221251, dated Nov. 10, 2022.
Notice of Allowance issued in U.S. Appl. No. 17/648,790, dated Feb. 28, 2023.
Office Communication issued in Japanese Patent Application No. 2018-550349, dated Mar. 7, 2023. (English translation).
Office Communication issued in U.S. Appl. No. 16/904,125, dated Mar. 23, 2023.
Office Communication issued in U.S. Appl. No. 17/096,932, dated Mar. 28, 2023.
Office Communication issued in U.S. Appl. No. 16/319,509, dated Apr. 10, 2023.
Brooks LA, Zander AC, Hansen CH, (2005). "Investigation into the feasibility of using a parametric array control source in an active noise control system," Proceedings of Acoustics 2005, Nov. 9-11, 2005. Australian Acoustical Society, pp. 39-45.
Ferraro, G.A. et al. (2012, E-pub Nov. 1, 2011). "Synergistic effects of cryolipolysis and shock waves for noninvasive body contouring." Aesthetic Plastic Surgery, 36(3), 666-679. 15 pages.
Krueger, N. et al. (2014). "Cryolipolysis for noninvasive body contouring: clinical efficacy and patient satisfaction." Clinical, Cosmetic and Investigational Dermatology, 7, 201-205.
Manstein, D. et al. "Selective Cryolysis: A Novel Method of Non-Invasive Fat Removal," Lasers in Surgery and Medicine: The Official Journal of the ASLMS, vol. 40, No. 9, Nov. 2008, pp. 595-604.
Chatterjee, D. et al. (2005). "Ultrasound-medicated destruction of contrast microbubbles used for medical imaging and drug delivery", Physics of Fluid 17, 100603. (8 pages).
Choudhary, S. et al. (2010, E-pub Jun. 12, 2010). "Lasers for tattoo removal: a review." Lasers Med Sci. Sep. 2010;25(5):619-627.
Fernandez, P. et al. (May 15, 2006). "A Master Relation Defines the Nonlinear Viscoelasticity of Single Fibroblasts." Biophysical Journal, 90(10):3796-3805.
Freund, et al. (2007). "A cumulative shear mechanism for tissue damage initiation in shock-wave lithotripsy." Ultrasound in Medicine and Biology. 33(9):1495-1503.
Kasza, K. E. et al. (2007). "The cell as a material." Current Opinion in Cell Biology, 19(1), 101-107.
Kossida et al. (2012). "Optical tattoo removal in a single laser session based on the method of repeated exposures," J. Am. Acad. Dermatology Feb. 2012. 66(2): 271-7.

\* cited by examiner

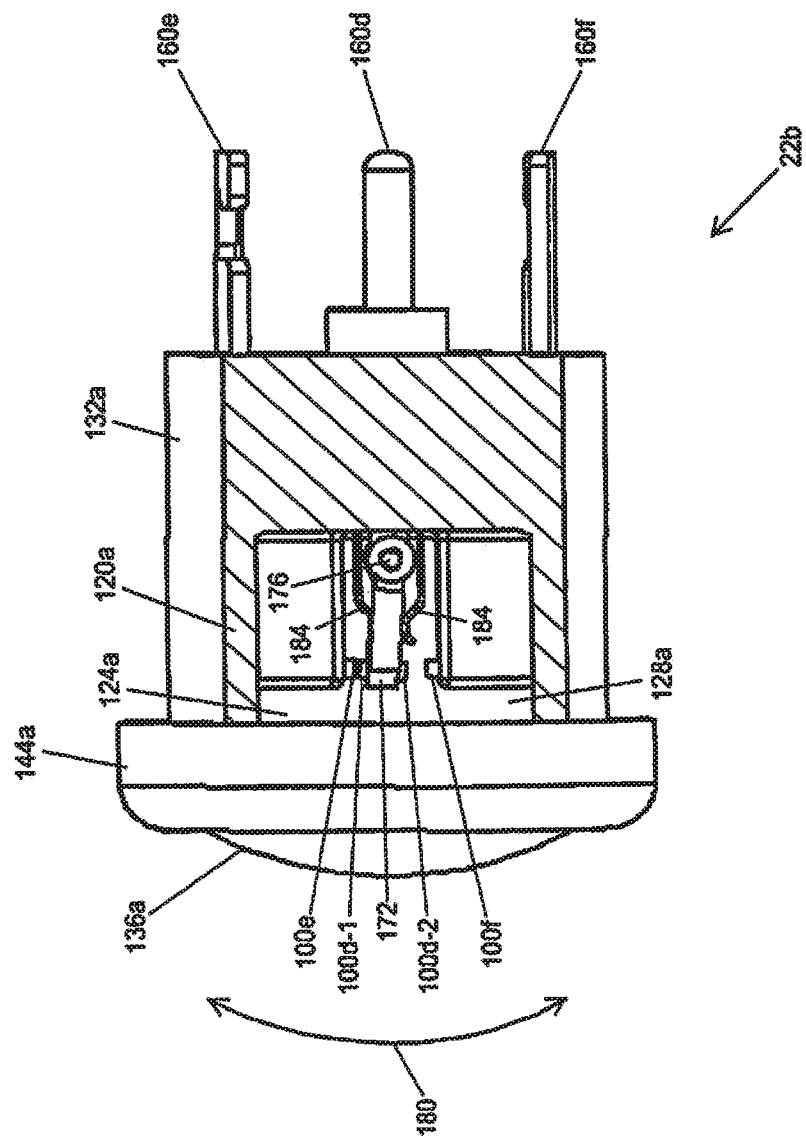

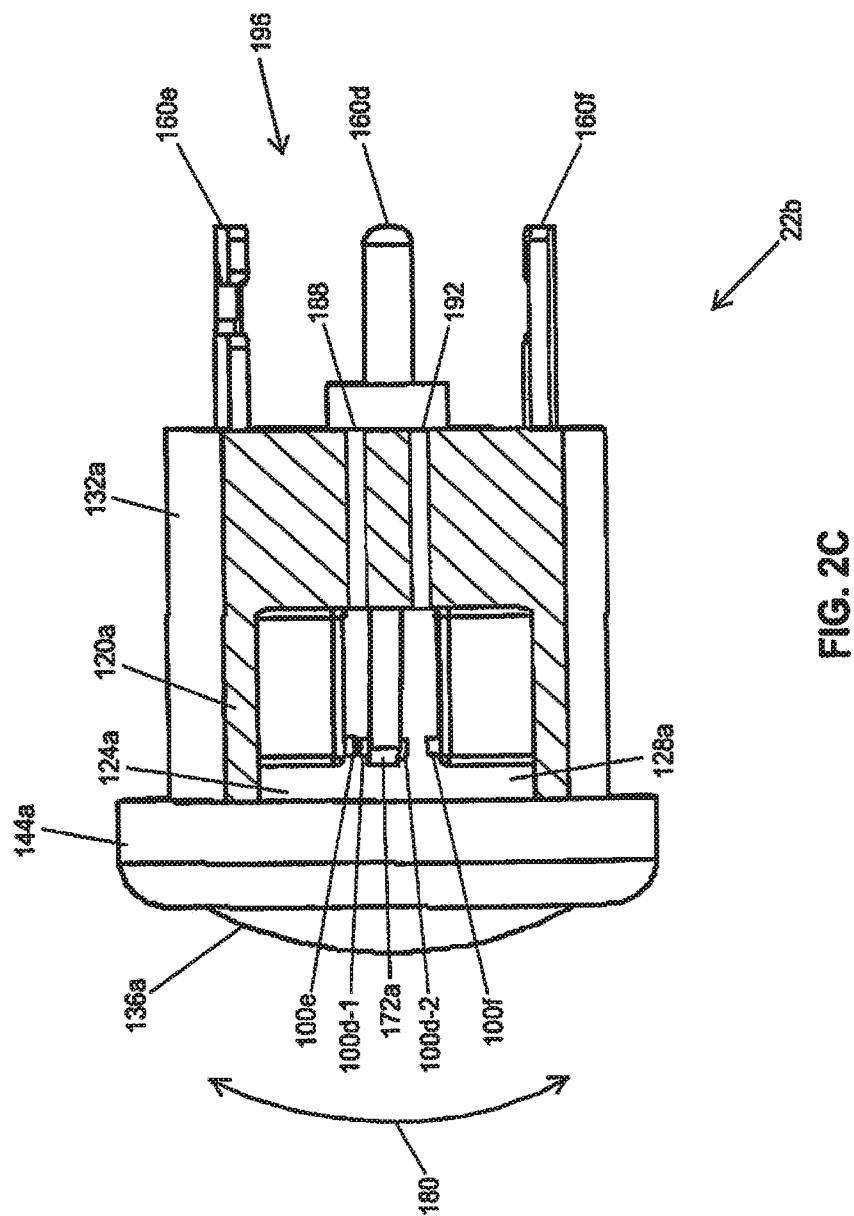

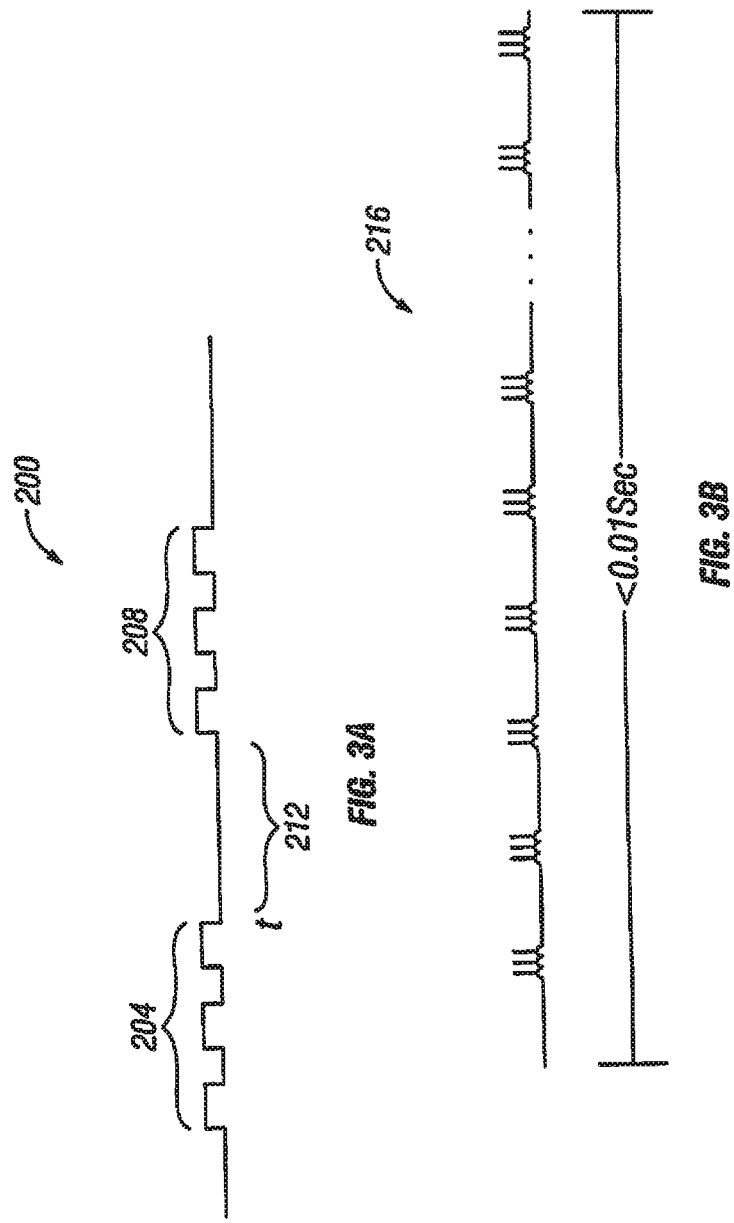

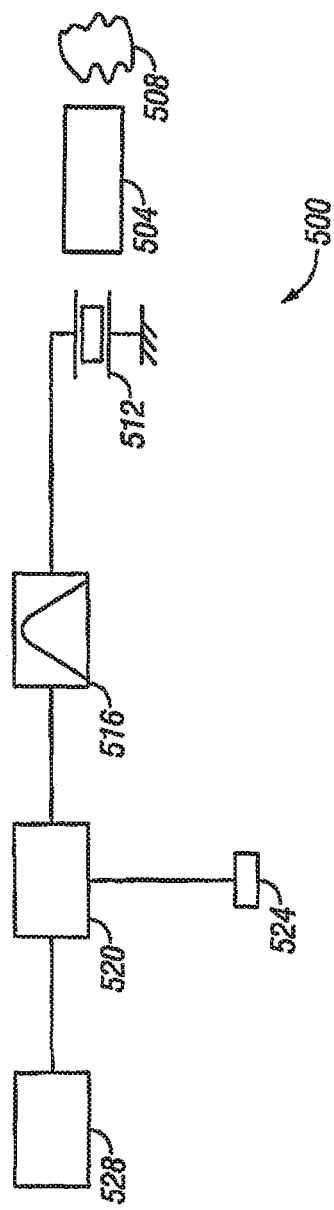

PULSED ACOUSTIC WAVE DERMAL CLEARING SYSTEM AND METHOD

CROSS-REFERENCE TO RELATED APPLICATIONS

This application is a national phase application under 35 U.S.C. § 371 of International Application No. PCT/US2017/023728 filed Mar. 23, 2017, which claims priority to U.S. Provisional Patent Application No. 62/312,372 filed Mar. 23, 2016, each of which applications is incorporated by reference in its entirety.

BACKGROUND

1. Field of the Invention

Embodiments of the present invention relate generally to therapeutic uses of shock waves. More particularly, but not by way of limitation, embodiments of the present invention relate to an apparatus for generating therapeutic shock waves (shock waves with therapeutic uses) for use in a dermal clearing system and applications of same.

2. Description of Related Art

Shockwaves have been used in certain medical and aesthetic therapies. "Shock wave" or "shockwave" is generally used to refer to an acoustic phenomenon (e.g., resulting from an explosion or lightning) that creates a sudden and intense change in pressure. These intense pressure changes can produce strong waves of energy that can travel through elastic media such as air, water, human soft tissue, or certain solid substances such as bone, and/or can induce an inelastic response in such elastic media. Methods for creating shock waves for therapeutic uses include: (1) electrohydraulic, or spark gap (EH); (2) electromagnetic, or EMSE; and (3) piezoelectric. Each is based upon its own unique physical principles.

A. Devices and Systems for Shockwave Generation

U.S. patent application Ser. No. 13/574,228 (a national-stage application of PCT/US20 11/021692, which published as WO 2011/091 020), by one of the present inventors, discloses a device for producing shock waves at a high pulse rate using a transducer. That device includes an acoustic-wave generator configured to emit acoustic waves having at least one frequency between 1 MHz and 1000 MHz; a shockwave housing coupled to the acoustic-wave generator; and a shockwave medium disposed in the shockwave housing; where the apparatus is configured such that if the acoustic-wave generator emits acoustic waves then at least some portion of the acoustic waves will travel through the shockwave medium and form shock waves. That device can be actuated to form shock waves configured to cause particles within a patient to rupture one or more cells of the patient, and the shock waves can be directed to cells of a patient such that the shock waves cause particles to rupture one or more of the cells. This acoustic-transducer device can produce high powered shockwaves at high frequencies or pulse rates.

Other systems for producing shockwaves can include an electrohydraulic (EH) wave generator. EH systems can generally deliver similar levels of energy as other methods, but may be configured to deliver that energy over a broader area, and therefore deliver a greater amount of shock wave energy to targeted tissue over a shorter period of time. EH systems generally incorporate an electrode (i.e., a spark plug) to initiate a shock wave. In EH systems, high energy shock waves are generated when electricity is applied to an electrode immersed in treated water contained in an enclosure. When the electrical charge is fired, a small amount of water is vaporized at the tip of the electrode and the rapid, nearly instantaneous, expansion of the vaporized water creates a shock wave that propagates outward through the liquid water. In some embodiments, the water is contained in an ellipsoid enclosure. In these embodiments, the shock wave may ricochet from the sides of the ellipsoid enclosure and converge at a focal point that coincides with the location of the area to be treated.

For example, U.S. Pat. No. 7,189,209 (the '209 Patent) describes a method of treating pathological conditions associated with bone and musculoskeletal environments and soft tissues by applying acoustic shock waves. The '209 Patent describes that shockwaves induce localized trauma and cellular apotosis therein, including micro-fractures, as well as to induce osteoblastic responses such as cellular recruitment, stimulate formation of molecular bone, cartilage, tendon, fascia, and soft tissue morphogens and growth factors, and to induce vascular neoangiogenesis. The '209 Patent claims several specific implementations of its method. For instance, the '209 Patent claims a method of treating a diabetic foot ulcer or a pressure sore, comprising: locating a site or suspected site of the diabetic foot ulcer or pressure sore in a human patient; generating acoustic shock waves; focusing the acoustic shock waves throughout the located site; and applying more than 500 to about 2500 acoustic shock waves per treatment to the located site to induce micro-injury and increased vascularization thereby inducing or accelerating healing. The '209 Patent discloses a frequency range of approximately 0.5-4 Hz, and application of about 300 to 2500 or about 500 to 8,000 acoustic shock waves per treatment site, which can result in a treatment duration for each treatment site and/or a "total time per treatment" for all sites that is inconveniently large. For example, the '209 Patent discloses total times per treatment for different examples ranging from 20 minutes to 3 hours.

U.S. Pat. No. 5,529,572 (the '572 Patent) includes another example of the use of electro-hydraulically generated shockwaves to produce therapeutic effect on tissues. The '572 Patent describes a method of increasing the density and strength of bone (to treat osteoporosis), comprising subjecting said bone to substantially planar, collimated compressional shock waves having a substantially constant intensity as a function of distance from a shock wave source, and wherein said collimated shock waves are applied to the bone at an intensity of 50-500 atmospheres. The '572 Patent describes the application of unfocussed shock waves to produce dynamic repetitive loading of the bone to increase mean bone density, and thereby strengthen bone against fracture. As described in the '572 Patent, "the unfocussed shock waves preferably are applied over a relatively large surface of the bone to be treated, for example to cover an area of from 10 to 150 $cm^2$. The intensity of the shock waves may be from 50-500 atmospheres. Each shock wave is of duration of a few microseconds, as in a conventional lithotripter, and is preferably applied at a frequency of 1-10 shock waves per second for a period of 5-30 minutes in each treatment. The number of treatments depends on the particular patient."

U.S. patent application Ser. No. 10/415,293 (the '293 Application), which is also published as US 2004/0006288, discloses another embodiment of the use of EH-generated shockwaves to provide a therapeutic effect on tissues. The '293 Application discloses a device, system, and method for the generation of therapeutic acoustic shock waves for at least partially separating a deposit from a vascular structure. The '293 Application describes that the device can produce shockwaves at a pulse rate of about 50 to about 500 pulses per minute (i.e., 0.83 to 8.33 Hz) with a number of pulses per treatment site (in terms of per length of vascular unit being treated) from about 100 to about 5,000 per 1 $cm^2$.

B. Shockwave Rate

Prior art literature has indicated that faster pulse rates using EH systems to provide shockwaves can lead to tissue damage. For example, in one study (Delius, Jordan, & et al, 1988) [2], the effect of shock waves on normal canine kidneys was examined in groups of dogs whose kidneys were exposed to 3000 shockwaves. The groups differed only in the rate of shockwave administration which was 100 Hz and 1 Hz, respectively. Autopsy was performed 24 to 30 hours later. Macroscopically and histologically, significantly more hemorrhages occurred in kidney parenchyma if shockwaves were administered at a rate of 100 Hz (vs 1 Hz). The results showed that kidney damage is dependent on the rate of shockwave administration.

In another study (Madbouly & et al, 2005) [7], slow shockwave lithotripsy rate (SWL) was associated with a significantly higher success rate at a lower number of total shockwaves compared to the fast shockwave lithotripsy rate. In this paper, the authors discussed how human studies have also shown a decrease in the incidence of SWL induced renal injury or need for anesthesia when slower rates of test SWL were used.

In yet another study (Gillitzer & et al, 2009) [5], slowing the delivery rate from 60 to 30 shockwaves per minute also provides a dramatic protective effect on the integrity of real vasculature in a porcine model. These findings support potential strategies of reduced pulse rate frequency to improve safety and efficacy in extracorporeal shockwave lithotripsy.

Soft tissues may transition from elastic to viscous behavior for pulse rates (PRs) between 1 Hz and 10 Hz. As a result, potential damage to tissue from shockwaves at pulse rates between 1 Hz and 10 Hz is unpredictable when typical lithotripsy power levels are used. Perhaps as a result, the prior art teaches slower pulse rates and large total times per treatment (TTPT). For example, currently known EH shockwave systems generally deliver pulse rates of less than 10 Hz and require large total times per treatment (TTPT) (e.g., TTPT periods of minutes or even hours for even a single treatment site). When, as may be typical, a treatment requires repositioning of a device at multiple treatment sites, the TTPT becomes large and potentially impractical for many patients and treatment needs.

While long treatment times may be acceptable for extracorporeal shockwave lithotripsy, the use of shockwaves to provide non-lithotripsy therapeutic effects on tissue in the medical setting is less than optimal if not impractical. For example, the cost of treatment often increases with the time needed to administer a treatment (e.g., due to the labor, facilities and other resource costs allocated to the administration of the treatment). Furthermore, in addition to costs, at some point the duration of providing treatment to the patient becomes unbearable for the patient receiving, and healthcare staff providing, the treatment.

C. Tissue as a Viscoelastic Material

One reason for sensitivity to pulse rate found in the prior art may be due in part to the relaxation time of tissue. Cells have both elastic and viscous characteristics, and thus are viscoelastic materials. Unlike most conventional materials, cells are highly nonlinear with their elastic modulus depending on the degree of applied or internal stress. (Kasza, 2007) [6]. One study (Fernandez (2006) [3] suggests that fibroblast cells can be modeled as a gel having a cross-linked actin network that show a transition from a linear regime to power law strain stiffening.

The authors of another paper (Freund, Colonius, & Evan, 2007) [4] hypothesize that the cumulative shear of the many shocks is damaging, and that the mechanism may depend on whether there is sufficient time between shocks for tissue to relax to the unstrained state. Their viscous fluid model suggested that any deformation recovery that will occur is nearly complete by the first 0.15 second after the shock. As a result, their model of the mechanism for cell damage would be independent of shock rate for shock rates slower than ~6 Hz. However, actual viscoelasticity of the interstitial material, with a relaxation time about 1 second, would be expected to introduce its sensitivity to the shock delivery rate. Assuming the interstitial material has a relaxation time of ~1 second, the authors would expect significantly decrease damage for delivery rates lower than ~1 Hz. Conversely, damage should increase for faster delivery rates. Implications of their model are that slowing delivery rates and broadening focal zones should both decrease injury.

D. Laser-Based Skin Treatment

In a another area of therapeutic medicine, the use of laser-based skin treatment has been used in tattoo removal, laser skin resurfacing, laser removal of birthmarks, laser removal of skin lesions, laser hair transplants or removal, laser scar removal, and a host of other various procedures. The body's natural reaction to each of these treatments present challenges to the efficacy of the treatment.

For example, in the context of tattoo removal, exposure of a tattooed area to a laser output currently creates a "whitening" condition within the treatment area that tends to reduce the effectiveness of subsequent laser exposures. During tattoo treatment, if the laser wavelength and power are appropriate to affect the tattoo, a "whitening" reaction typically occurs. The immediate whitening reaction is a result of the generation of vacuoles due to rapid heating or energy transfer associated with laser exposure to the tattoo pigment particle. The dermal vacuoles associated with whitening result in the attenuation or scattering of laser light resulting in loss of the lasers effectiveness after the initial treatment. Furthermore, the dermal vacuoles remain in the skin for a period of time limiting the effectiveness of subsequent laser exposures in the same session Laser generated dermal vacuoles are generally located at the epidermis-dermis boundary and around individual pigment particle clusters.

The vacuoles located at the epidermis-dermis boundary are thought to be produced by localized heating from the laser light absorption by melanin in the epidermis. The vacuoles located around the pigment particle agglomerations are believed to be a direct result of the rapid heating from the laser light absorption of the pigment particle aggregation within the dermis.

Post-laser whitening reaction may fade over about twenty minutes or more following the last laser exposure. Such fading may be evidenced by the resolution of the superficial vacuoles caused by the dissipation and absorption of vacuole contents, including gas, over time.

Whitening is problematic at least in part because the presence of dermal vacuoles in the treatment area caused by the first laser pass may attenuate or weaken the delivery of light in one or more subsequent laser passes. For example, light impinging on vacuoles may scatter in multiple directions, including away from the treatment area. Thus, vacuole presence reduces laser therapy effectiveness.

Currently, the primary approach for removing tattoos is through the use of lasers. However, after a single laser treatment of the tattoo site, the laser is no longer effective for aforementioned reasons. As a result, to remove a tattoo using a laser, multiple sessions over many months are required.

There is a great desire to speed up the tattoo removal process. To do so, repeated laser treatments of the tattoo site within the same day have been explored. One approach, call the R20 method, treats a tattoo site with a laser wherein the laser treatments are spaced at least 20 minutes apart so as to allow the vacuoles to be reabsorbed at the site. (See, e.g., Kossida et al, Optical tattoo removal in a single laser session based on the method of repeated exposures, J. Am. Acad. Dermatology 2012 February. 66(2): 271-7.) For a busy practice, this approach is not practical since it requires the patient to be in the office for long periods of time.

More recently, to overcome this problem, U.S. patent application Ser. No. 13/753,816 (the '816 Application), which is also published as US 2013/0165839, discloses the use of perfluorodecalin (PFD) to inhibit or reduce whitening caused by laser treatment of tattoos. The '816 Application discloses that by using PFD on the affected skin, lasers can be applied in quick succession without waiting for 20 minutes.

PFD is a liquid that is a colorless, inert compound with low surface tension and insoluble in blood and water. Unfortunately, PFD has very poor dermal penetration. As a result it is used extensively in cosmetics. As a result, PFD is good at reducing whitening that is caused by vacuoles located superficially (e.g., epidermal-dermal boundary). However, due to its poor dermal penetration, vacuoles that surround and shield the previously treated intradermal pigment particles, are not affected. Thus, while PFD provides benefits in reducing the appearance of whitening, it only provides limited benefit in improving the effectiveness of repeated laser treatments to the tattoo site.

SUMMARY

Embodiments of the present methods, apparatuses, and systems can be configured to provide dermal clearing by dispersing and/or eliminating dermal vacuoles located superficially and/or deeper in the dermis (e.g. adjacent to pigment particle agglomerations), as well as vacuoles in the epidermis. The present methods, apparatuses, and systems can thereby enable more effective repeated laser treatments over the same treatment area in quick succession.

Some embodiments of the present methods (e.g., for acoustic treatment of tissue to disperse vacuoles within the tissue) comprise: identifying the location of tissue containing vacuoles; coupling an acoustic wave generator to the tissue containing the vacuoles; and directing pulsed acoustic waves from the acoustic wave generator into the tissue containing the vacuoles.

In some embodiments of the present methods, the tissue containing vacuoles has previously been treated with a laser.

Some embodiments of the present methods further comprise: treating the skin containing vacuoles with a laser after directing pulsed acoustic waves from the acoustic wave generator into the tissue containing the vacuoles. In some embodiments, the skin is treated with an acoustic wave generator for between about 0.1 minute and about 10 minutes. In some embodiments, the laser treatment comprises applying a laser with a pulse duration of between about 1 nanosecond and about 1 microsecond to the targeted skin. In some embodiments, the laser comprises a Q-switched laser or a pico-second laser.

In some embodiments of the present methods, the laser treatment comprises tattoo removal, laser skin resurfacing, laser removal of birthmarks, laser removal of skin lesions, laser hair transplants, laser scar removal, laser-assisted hair reduction, laser removal of vascular lesions, laser lip lightening, and/or laser treatment of melisma.

Some embodiments of the present methods further comprise: treating the skin containing vacuoles with a laser after directing pulsed acoustic waves from the acoustic wave generator into the tissue containing the vacuoles; and repeating directing and treating in alternating fashion for at least 2 iterations in a single treatment session. In some embodiments, treating the skin containing vacuoles with a laser is performed within 10 minutes of directing the pulsed acoustic waves. In some embodiments of the present methods, at least two subsequent iterations of directing the pulsed acoustic waves are performed within 10 minutes or less.

Some embodiments of the present systems (e.g., dermal clearing systems) comprise: a pulsed acoustic wave generator configured to generate pulsed acoustic waves and direct the generated waves to skin to clear epidermal and intradermal vacuoles.

In some embodiments of the present systems, the generated acoustic waves have a frequency between about 700 KHz and about 100 Mhz.

In some embodiments of the present systems, the generated acoustic waves have a pulse duration between about 1 nanosecond and about 1 microsecond.

In some embodiments of the present systems, the generated acoustic waves have a pulse rate between about 10 Hz and about 1 KHz.

In some embodiments of the present systems, the Mechanical Index MI of the generated waves is between about 0.15 to about 1.9.

In some embodiments of the present systems, the pulsed acoustic wave generator includes a rapid pulse electrohydraulic shockwave generator that comprises: a housing defining a chamber and a shockwave outlet; a medium disposed in the chamber; a plurality of electrodes and capacitors configured to be disposed in the chamber to define one or more spark gaps; and a pulse-generation system configured to apply voltage pulses to the plurality of electrodes and capacitors in the chamber.

In some embodiments of the present systems, the pulsed acoustic wave generator is configured to generate the acoustic waves in pulses at a rate of between about 10 Hz and about 5 MHz.

In some embodiments of the present systems, the pulsed acoustic wave generator includes a megasonic wave generator. In some embodiments, the megasonic wave generator is configured to produce pulsed acoustic waves with a frequency between about 700 KHz and about 20 Mhz. In some embodiments, the megasonic wave generator is configured to produce pulsed acoustic waves with a pulse duration between about 1 nanosecond and about 1 microsecond. In some embodiments, the megasonic wave generator is configured to produce pulsed acoustic waves with a pulse rate between about 10 Hz and about 1 KHz. In some embodiments, the power of the megasonic wave generator is set so that the Mechanical Index (MI) is between about 0.15 to 1.8.

In some embodiments of the present systems, the rapid pulse electrohydraulic generator is set so that the peak pressure output is between about 0.8 MPa and 20 MPa The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system or apparatus that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Further, a structure (e.g., a component of an apparatus) that is configured in a certain way is configured in at least that way, but it can also be configured in other ways than those specifically described.

Any embodiment of any of the present systems, apparatuses, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

Details associated with the embodiments described above and others are presented below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The figures are drawn to scale (unless otherwise noted), meaning the sizes of the depicted elements are accurate relative to each other for at least the embodiment depicted in the figures.

FIG. 2B depicts a cutaway side view of a second embodiment of a removable spark head usable with embodiments of the present handheld probes, such as the one of FIG. 2.

FIG. 2C depicts a cutaway side view of a third embodiment of a removable spark head usable with embodiments of the present handheld probes, such as the one of FIG. 2.

FIG. 3A-3B depict a timing diagrams of one example of the timed application of energy cycles or voltage pulses in the system of FIG. 1 and/or the handheld probe of FIG. 2.

FIG. 6 depicts a block diagram of an embodiment of a radio-frequency (RF) powered acoustic ablation system.

Figure 1:
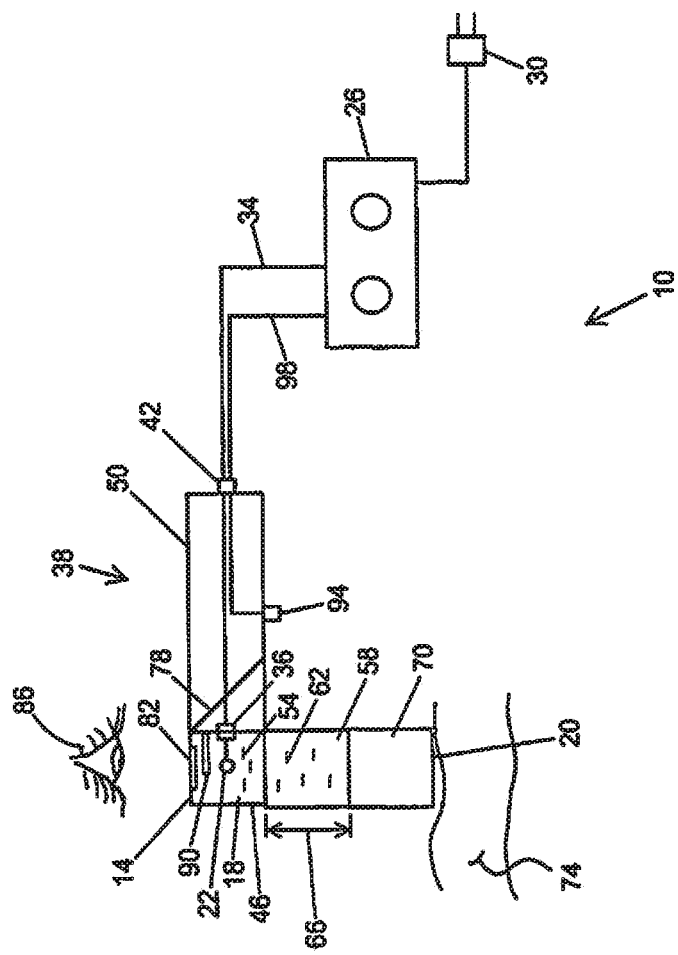
FIG. 1 depicts a block diagram of a first embodiment of the present electro-hydraulic (EH) shockwave generating systems.

It should be understood that the drawings are not necessarily to scale and that the disclosed embodiments are sometimes illustrated diagrammatically and in partial views. In certain instances, details which are not necessary for an understanding of the disclosed methods and apparatuses or which render other details difficult to perceive may have been omitted. It should be understood, of course, that this disclosure is not limited to the particular embodiments illustrated herein.

DESCRIPTION OF ILLUSTRATIVE EMBODIMENTS

Certain embodiments of the present systems and apparatuses are configured to generate high-frequency shock waves in a predictable and consistent manner. In some embodiments, the generated EH shock waves can be used in medical and/or aesthetic therapeutic applications (e.g., when directed at and/or delivered to target tissue of a patient). Examples of medical and/or aesthetic therapeutic applications in which the present systems can be used are disclosed in: (1) U.S. patent application Ser. No. 13/574,228, published as US 2013/0046207; (2) U.S. patent application Ser. No. 13/547,995, published as, published as US 2013/0018287; (3) U.S. patent application Ser. No. 13/798,710, published as US 2014/0257144; and (4) PCT/US2014/021746 all of which are incorporated here in their entireties. The EH shock waves generated by the present systems can be configured to impose sufficient mechanical stress to rupture cells of the target tissue (e.g., through membrane-degradation damage).

When targeted cells (cells of target tissue) are exposed to the generated high-pulse rate shockwaves, the cells experience sharp gradients of mechanical stress due to the spatial heterogeneity parameters of the cells, such as density and shear elasticity modulus of the different components of the cell. For instance, dense and/or inelastic components inside a cell undergo greater mechanical stress when subjected to shock waves as compared to lighter components. In particular, acceleration of higher-density particles or components within the cellular structure exposed to the impact front is typically very large. At the same time, the impact on lower-density biological structures making up the cell structure when exposed to such a large gradient of pressure is significantly reduced because the elasticity of the lower-density biological structures allows them to generally act as low-compliance material. The difference in mechanical stress results in movement of the dense and/or inelastic components within the cell.

When the cell is exposed to repeated shock waves at a certain frequency and energy level, the dense and/or inelastic components are repeatedly moved until they break out of the cell, thereby rupturing the cell. In particular, the properties mismatch of the cellular structure and cells' ability to experience deformation when exposed to the impact front lead to cellular destruction as described. One possible theory to explain the phenomenon of rupturing cellular structure can be found in (Burov, V. A., 2002) [1], which is incorporated herein by reference in its entirety.

As discussed by Burov [1], while a cell may oscillate as an integral unit when impacted by these pressure fronts, sharp gradients of mechanical stress can be generated inside the cell as a result of spatial heterogeneity parameters (i.e., density and shear elasticity modulus). This concept can be illustrated by modeling the biological structure as two linked balls with masses $m_1$ and $m_2$ and the density $(\rho_0)$ of the liquid oscillating around the balls with the speed $\mu_o(t)$ differ insignificantly from the densities of the balls (by $\rho_1$ and $\rho_2$ respectively). If only the resistance to potential flow is taken into account, the force applied to the link is calculated as shown in Equation (1):

$$F = \frac{2}{3} \frac{m_1 m_2}{m_1 + m_2} \frac{[\rho_1 - \rho_2]}{\rho_0} \mu_0(t) \quad (1)$$

Additional discussions of Equation (1) and its variables are further provided in [1]. For example, if the ball radius (R) is about 10 μm and the difference between the densities of the balls is 0.1 $\rho_0$, and results in a stress force, $F/(\pi R^2)m$ of $10^9$ dyne/cm$^2$. This is sufficient to rupture a cell membrane. The embodiments of the present apparatuses generate shock waves in a controlled manner that can be used to cause targeted damage to certain cells, which have medical and/or aesthetic therapeutic applications that are discussed further below.

Another possible theory to explain the phenomenon of cell rupturing is the accumulation shear stress in the denser material in the cellular structure. In heterogeneous media, such as cells with particles (e.g., pigment particles), shock waves cause the cell membranes to fail by a progressive (i.e., accumulated) shearing mechanism. On the other hand, in homogeneous media, compression by shock waves causes minimal, if any, damage to membranes. Microscopic focusing and defocusing of the shock wave as it passes through the heterogeneous media can result in shock wave strengthening or weakening locally that result in an increase in local shearing. Relative shearing motion of the cell membrane occurs on the scale of the heterogeneities of the cellular structure. It is believed that when shock waves strike a region of heterogeneities (e.g., cells containing particles), the particle motion that is out of phase with the incoming waves generates cell disruptive energy transfer (e.g., shear stress). The out of phase motion (e.g., shear stress) causes microscopic damage to the cell membrane that can progressively grow into cell membrane failure with additional successive accumulation of shear stress.

The progressive shearing mechanism of repeated exposure to shock waves can be considered dynamic fatigue of the cell membranes. Damage from dynamic fatigue is dependent on three factors: (1) applied stress or strain, (2) the rate at which the strain is applied, and (3) accumulated number of strain cycles. These three factors can be manipulated to cause a cell with heterogeneities to experience catastrophic cell membrane failure as compared to a relatively more homogeneities at a particular applied strain, strain rate, and strain cycles.

The manipulation of the factors can be done by providing EH shock waves of certain properties, such as the number of shock waves, the amount of time between each shock wave, and the strength of the applied shock waves. As discussed above, if there is enough time between shock waves for the tissue to relax to its unstrained state, the cells will become more resistant to failure. As such, in an embodiment for an EH system, shock waves at a pulse rate greater than 5 Hz and greater than 100 Hz and greater than 1 MHz are delivered to the targeted cellular structures to achieve dynamic fatigue of the tissue and not allow the tissue time to relax.

A third possible theory is that the EH shock waves cause a combination of effects of direct movement of the particles contained in the cellular structure and dynamic fatigue that rupture the cells. While particle-containing cells are an apparent example of cellular structures exhibiting heterogeneities, their description is not intended to limit the scope of the present disclosure. Instead, the embodiments disclosed herein can be used to rupture or cause damage to other cellular structures that exhibit heterogeneities, such as cellular structures that have different effective density regions. The parameters of the shock waves generated according to the disclosed aspects can be adjusted based, at least, on the regions of different effective densities (i.e. heterogeneities) to cause cellular damage as described herein. Heterogeneities can be regions within a single cell, a region of different types of cells, or a combination of both. In certain embodiments, a region of heterogeneity within a cell includes a region having an effective density greater than the effective density of the cell. In one specific example, the effective density of a fibroblast cell is about 1.09 g/cm$^3$, a region of heterogeneity in the cell would be particles contained within the cell that have an effective density greater than 1.09 g/cm², such as graphite with a density of 2.25 g/cm³. In certain embodiments, a region of cellular heterogeneity between cells includes a region with different types of cells, where each cell type has a different effective density, such as fibroblast cells and fat cells or hair follicles. The present disclosure provides further examples of cellular structures containing heterogeneities below.

Referring now to the drawings, and more particularly to FIG. 1, shown therein and designated by the reference numeral 10 is a block diagram of one embodiment of the present apparatuses or systems for electro-hydraulically generating shockwaves in a controlled manner. In some embodiments, such as the one shown, system 10 includes a handheld probe (e.g., with a first housing, such as in FIG. 2) and a separate controller or pulse-generation system (e.g., in or with a second housing coupled to the handheld probe via a flexible cable or the like). In other embodiments, the present systems include a single handheld apparatus disposed in a single housing.

In the embodiment shown, apparatus 10 comprises: a housing 14 defining a chamber 18 and a shockwave outlet 20; a liquid (54) disposed in chamber 18; a plurality of electrodes (e.g., in spark head or module 22) configured to be disposed in the chamber to define one or more spark gaps; and a pulse-generation system 26 configured to apply voltage pulses to the electrodes at a rate of between 10 Hz and 5 MHz. In this embodiment, the capacitive/inductive coil system 26 is configured to apply the voltage pulses to the electrodes such that portions of the liquid are vaporized to propagate shockwaves through the liquid and the shockwave outlet.

In the embodiment shown, pulse-generation system 26 is configured for use with an alternating current power source (e.g., a wall plug). For example, in this embodiment, pulse-generation system 26 comprises a plug 30 configured to be inserted into a 110V wall plug. In the embodiment shown, pulse-generation system 26 comprises a capacitive/inductive coil system, on example of which is described below with reference to FIG. 6. In other embodiment, pulse-generation system 26 can comprise any suitable structure or components configured to apply high voltages to the electrodes in a periodic fashion to generate electric sparks of sufficient power to vaporize liquid in the respective spark gaps, as described in this disclosure.

In the embodiment shown, pulse-generation system 26 is (e.g., removably) coupled to the electrodes in spark head or module 22 via a high-voltage cable 34, which may, for example, include two or more electrical conductors and/or be heavily shielded with rubber or other type of electrically insulating material to prevent shock. In some embodiments, high-voltage cable 34 is a combined tether or cable that further includes one or more (e.g., two) liquid lumens through which chamber 18 can be filled with liquid and/or via which liquid can be circulated through chamber 18 (e.g., via combined connection 36). In the embodiment shown, apparatus 10 comprises a handheld probe or handpiece 38 and cable 34 is removably coupled to probe 38 via a high-voltage connector 42, which is coupled to spark head or module 22 via two or more electrical conductors 44. In the embodiment shown, probe 38 comprises a head 46 and a handle 50, and probe 38 can comprise a polymer or other electrically insulating material to enable an operator to grasp handle 50 to position probe 38 during operation. For example, handle 50 can be molded with plastic and/or can be coated with an electrically insulating material such as rubber.

In the embodiment shown, a liquid 54 (e.g., a dielectric liquid such as distilled water) is disposed in (e.g., and substantially fills) chamber 18. In this embodiment, spark head 22 is positioned in chamber 18 and surrounded by the liquid such that the electrodes can receive voltage pulses from pulse-generation system 26 (e.g., at a rate of between 10 Hz and 5 MHz) such that portions of the liquid are vaporized to propagate shockwaves through the liquid and shockwave outlet 20. In the embodiment shown, probe 38 includes an acoustic delay chamber 58 between chamber 18 and outlet 20. In this embodiment, acoustic delay chamber is substantially filled with a liquid 62 (e.g., of the same type as liquid 54) and has a length 66 that is sufficient to permit shockwaves to form and/or be directed toward outlet 20. In some embodiments, length 66 may be between 2 millimeters (mm) and 25 millimeters (mm). In the embodiment shown, chamber 18 and acoustic-delay chamber 58 are separated by a layer of sonolucent (acoustically permeable or transmissive) material that permits sound waves and/or shockwaves to travel from chamber 18 into acoustic-delay chamber 58. In other embodiments, liquid 62 may be different than liquid 54 (e.g., liquid 62 may comprise bubbles, water, oil, mineral oil, and/or the like). Certain features such as bubbles may introduce and/or improve a nonlinearity in the acoustic behavior of liquid 54 to increase the formation of shockwaves. In further embodiments, chamber 18 and acoustic-delay chamber 54 may be unitary (i.e., may comprise a single chamber). In further embodiments, acoustic-delay chamber 54 may be replaced with a solid member (e.g., a solid cylinder of elastomeric material such as polyurethane). In the embodiment shown, probe 38 further includes an outlet member 70 removably coupled to the housing at a distal end of the acoustic delay chamber, as shown. Member 70 is configured to contact tissue 74, and can be removed and either sterilized or replaced between patients. Member 70 comprises a polymer or other material (e.g., low-density polyethylene or silicone rubber) that is acoustically permeable to permit shockwaves to exit acoustic-delay chamber 58 via outlet 20. Tissue 74 may, for example, be human skin tissue to be treated with apparatus 10, and may, for example, include a tattoo, a blemish, a subdermal lesion, or a basal cell abnormality. In some embodiments, an acoustic coupling gel (not shown) may be disposed between member 70 and tissue 74 to lubricate and provide additional acoustic transmission into tissue 74.

In the embodiment shown, probe 38 includes an acoustic mirror 78 that comprises a material (e.g., glass) and is configured to reflect a majority of sound waves and/or shock waves that are incident on the acoustic mirror. As shown, acoustic mirror 58 can be angled to reflect sound waves and/or shockwaves (e.g., that originate at spark head 22) toward outlet 20 (via acoustic-delay chamber). In the embodiment shown, housing 14 can comprise a translucent or transparent window 82 that is configured to permit a user to view (through window 82, chamber 18, chamber 58, and member 70) a region of a patient (e.g., tissue 74) comprising target cells (e.g., during application of shockwaves or prior to application of shockwaves to position outlet 20 at the target tissue). In the embodiment shown, window 82 comprises an acoustically reflective material (e.g., glass) that is configured to reflect a majority of sound waves and/or shock waves that are incident on the window. For example, window 82 can comprise clear glass of sufficient thickness and strength to withstand the high-energy acoustic pulses produced at spark head 22 (e.g., tempered plate glass having a thickness of about 2 mm and an optical transmission efficiency of greater than 50%).

In FIG. 1, a human eye 86 indicates a user viewing the target tissue through window 82, but it should be understood that target tissue may be "viewed" through window 82 via a camera (e.g., a digital still and/or video camera). By direct or indirect observation, acoustic energy can be positioned, applied, and repositioned according to target tissues, such as extant tattoos, and by indications of acoustic energy, such as a change in the color of the tissue. However, if spark head 22 is disposed where a user can view spark head 22, the brightness of the resulting spark from spark head 22 may be too bright for a user to comfortably view, and in the embodiment shown, probe 38 is configured such that the plurality of electrodes are not visible to a user viewing a region (e.g., of target tissue) through window 82 and outlet 20. For example, in the embodiment shown, probe 38 includes an optical shield 90 disposed between spark head 22 and window 82. Shield 90, for example, can have a width and/or a length that are less than a corresponding width and/or length of window 82 such that shield 90 is large enough to substantially block light from spark head 22 from traveling directly to the user's eye, but does not interfere with the field-of-view through window 82 and outlet 20 more than is necessary to block that light. Shield 90 can, for example, comprise a thin sheet of metal, such as stainless steel, or other opaque material, or can comprise welder's glass (e.g., an LCD darkened by a photocell or other light-sensitive material) that is optically activated and darkened by the brightness of sparks at the spark gaps. The acoustic effect of shielding the resulting sparks from a spark gap head must be considered in order to maintain the effect of a point source from spark head 22 and a resulting desired planar wavefront. If shield 90 comprises an acoustically reflective material, to prevent pulse broadening, the distance between the shield and the spark gaps between electrodes in spark head 22 may be selected to minimize (e.g., at least destructive) interference between sound waves and/or shockwaves reflected from the shield and sound waves and/or shockwaves originating at spark head 22 (e.g., such that intersecting waves do not produce excess echoes or reverberation). With a velocity of sound waves in a medium such as distilled water of about 1500 m/Sec, the distance between the spark head and the shield may be calculated to be at ½ and ¾ wavelengths from the source.

Spark head 22 (e.g., the electrodes in spark head 22) may have a limited lifetime that may be extended by limiting the duration of activation. In the embodiment shown, apparatus 10 includes a switch or trigger 94 coupled to pulse-generation system 26 via a switch wire or other connection 98 through connector 42, such that switch 94 can be actuated to apply voltage pulses to the electrodes in spark head 22.

Figure 2:
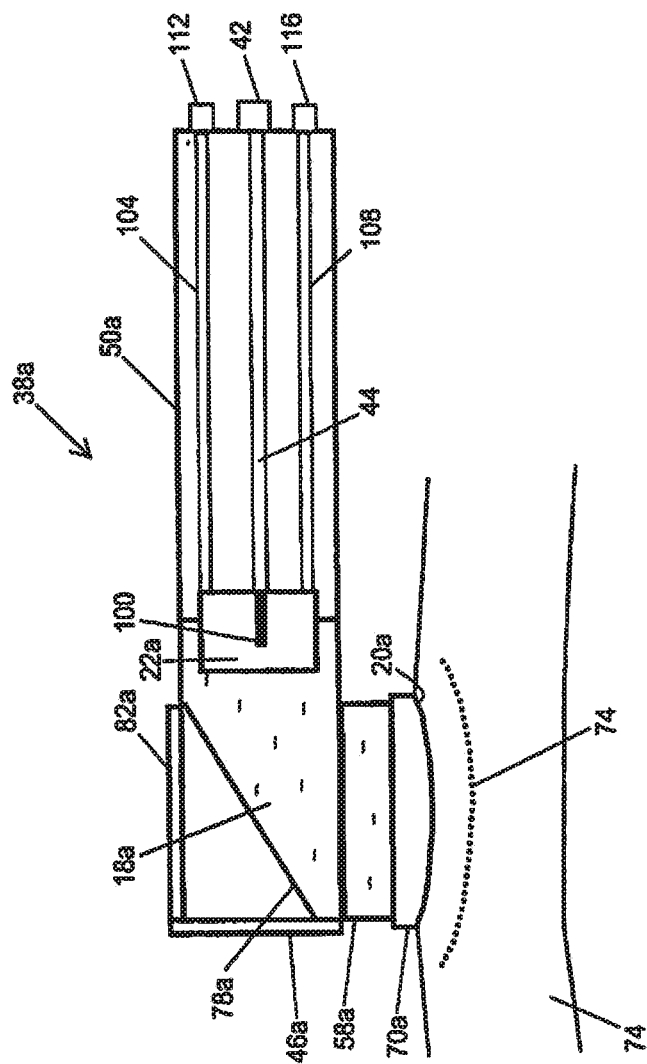
FIG. 2 depicts a cross-sectional side view of a handheld probe for some embodiments of the present EH shockwave generating systems.

FIG. 2 depicts a cross-sectional side view of a second embodiment 38a of the present handheld probes or handpiece for use with some embodiments of the present EH shockwave generating systems and apparatuses. Probe 38a is substantially similar in some respects to probe 38, and the differences are therefore primarily described here. For example, probe 38a is also configured such that the plurality of electrodes of spark head or module 22a are not visible to a user viewing a region (e.g., of target tissue) through window 82a and outlet 20a. However, rather than including an optical shield, probe 38a is configured such that spark head 22a (and the electrodes of the spark head) are offset from an optical path extending through window 82a and outlet 20a. In this embodiment, acoustic mirror 78a is positioned between spark head 22a and outlet 20a, as shown, to define a boundary of chamber 18a and to direct acoustic waves and/or shockwaves from spark head 22a to outlet 20a. In the embodiment shown, window 82a can comprise a polymer or other acoustically permeable or transmissive material because acoustic mirror 78a is disposed between window 82a and chamber 18a and sound waves and/or shockwaves are not directly incident on window 82a (i.e., because the sound waves and/or shock waves are primarily reflected by acoustic mirror 78a).

In the embodiment shown, spark head 22a includes a plurality of electrodes 100 that define a plurality of spark gaps. The use of multiple spark gaps can be advantageous because it can double the number of pulses that can be delivered in a given period of time. For example, after a pulse vaporizes an amount of liquid in a spark gap the vapor must either return to its liquid state or must be displaced by a different portion of the liquid that is still in a liquid state. In addition to the time required for the spark gap to be re-filled with water before a subsequent pulse can vaporize additional liquid, sparks also heat the electrodes. As such, for a given spark rate, increasing the number of spark gaps reduces the rate at which each spark gap must be fired and thereby extends the life of the electrodes. Thus, ten spark gaps potentially increases the possible pulse rate and/or electrode life by a factor of ten.

As noted above, high pulse rates can generate large amounts of heat that may increase fatigue on the electrodes and/or increase the time necessary for vapor to return to the liquid state after it is vaporized. In some embodiments, this heat can be managed by circulating liquid around the spark head. For example, in the embodiment of FIG. 2, probe 38 includes conduits 104 and 108 extending from chamber 18a to respective connectors 112 and 116, as shown. In this embodiment, connectors 112 and 116 can be coupled to a pump to circulate liquid through chamber 18a (e.g., and through a heat exchanger. For example, in some embodiments, pulse-generation system 26 (FIG. 1) can comprise a pump and a heat exchanger in series and configured to be coupled to connectors 112 and 116 via conduits or the like. In some embodiments, a filter can be included in probe 38a, in a spark generation system (e.g., 26), and/or between the probe and the spark generation system to filter liquid that is circulated through the chamber Additionally, due to the limited life of electrodes 100 at high pulse rates, some embodiments of the present probes may be disposable. Alternatively, some embodiments are configured to permit a user to replace the electrodes. For example, in the embodiment of FIG. 2, spark head 22a is configured to be removable from probe 38a. For example, spark head 22a may be removable through handle 50a, or handle 50a may be removably coupled (e.g., via threads or the like) to head 46a such that upon removal of handle 50a from head 46, spark head 22a can be removed from head 46a and replaced.

As illustrated in FIG. 2, application of each shockwave to a target tissue includes a wavefront 118 propagating from outlet 20a and traveling outward through tissue 74. As shown, wavefront 74 is curved according to its expansion as it moves outwardly and partially according to the shape of the outer surface of outlet member 70a that contacts tissue 74. In other embodiments, such as that of FIG. 1, the outer shape of the contact member can be planar or otherwise shaped to affect certain properties of the wavefront as it passes through outlet 20a and propagates through the target tissue.

Figure 2A:
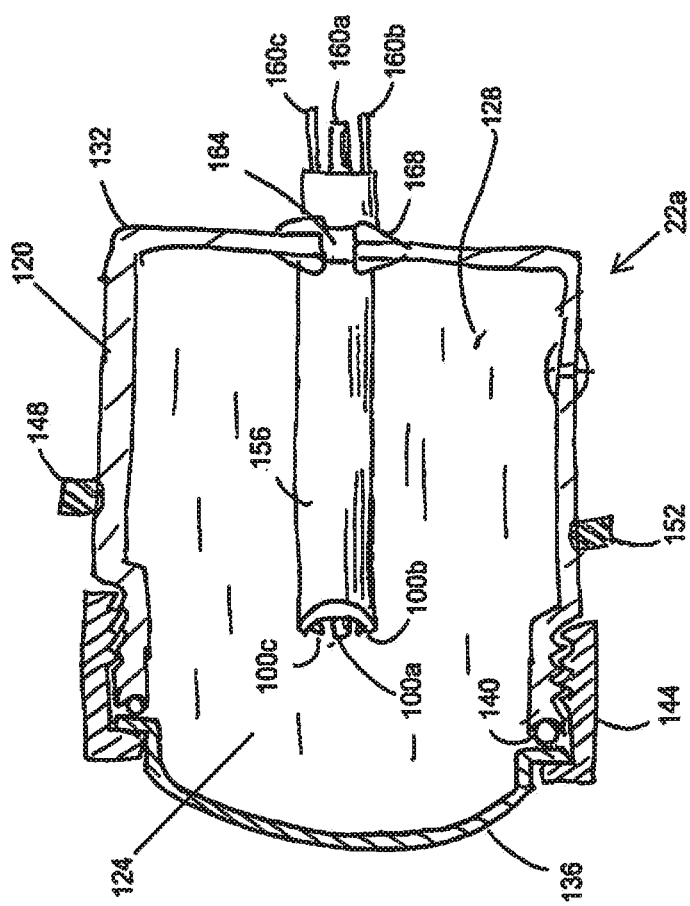
FIG. 2A depicts a cross-sectional side view of a first embodiment of a removable spark head usable with embodiments of the present handheld probes, such as the one of FIG. 2.

FIG. 2A depicts an enlarged cross-sectional view of first embodiment of a removable spark head or module 22a. In the embodiment shown, spark head 22a comprises a sidewall 120 defining a spark chamber 124, and a plurality of electrodes 100a, 100b, 100c disposed in the spark chamber. In the embodiment shown, spark chamber 124 is filled with liquid 128 which may be similar to liquid 54 (FIG. 1). At least a portion of sidewall 120 comprises an acoustically permeable or transmissive material (e.g., a polymer such as polyethylene) configured to permit sound waves and/or shockwaves generated at the electrodes to travel through sidewall 120 and through chamber 18a. For example, in the embodiment shown, spark head 22a includes a cup-shaped member 132 that may be configured to be acoustically reflective and an acoustically permeable cap member 136. In this embodiment, cap member 136 is dome shaped to approximate the curved shape of an expanding wavefront that originates at the electrodes and to compress the skin when applied with moderate pressure. Cap member 136 can be coupled to cup-shaped member 132 with an O-ring or gasket 140 and a retaining collar 144. In the embodiment shown, cup-shaped member 132 has a cylindrical shape with a circular cross-section (e.g., with a diameter of 2 inches or less). In this embodiment, cup-shaped member includes bayonet-style pins 148, 152 configured to align with corresponding grooves in head 46a of probe 38a (FIG. 2) to lock the position of spark head 22a relative to the probe.

In the embodiment shown, an electrode core 156 having conductors 160a, 160b, 160c and extending through aperture 164, with the interface between aperture 164 and electrode core 156 sealed with a grommet 168. In the embodiment shown, a central conductor 160a extends through the center of core 156 and serves as a ground to corresponding center electrode 100a. Peripheral conductors 160b, 160c are in communication with peripheral electrodes 100b, 100c to generate sparks across the spark gap between electrodes 100a and 100b, and between electrodes 100a and 100c. It should be understood that while two spark gaps are shown, any number of spark gaps may be used, and may be limited only by the spacing and size of the spark gaps. For example, other embodiments include 3, 4, 5, 6, 7, 8, 9, 10, or even more spark gaps.

FIG. 2B depicts an enlarged cutaway side view of a second embodiment of a removable spark head or module 22b. In the embodiment shown, spark head or module 22b comprises a sidewall 120a defining a spark chamber 124a, and a plurality of electrodes 100d-1, 100d-2, 100, 100f disposed in the spark chamber. In the embodiment shown, spark chamber 124a is filled with liquid 128a which may be similar to liquid 128 and/or 54. At least a portion of sidewall 120a comprises an acoustically permeable or transmissive material (e.g., a polymer such as polyethylene) configured to permit sound waves and/or shockwaves generated at the electrodes to travel through sidewall 120a and through chamber 18a (FIG. 2). For example, in the embodiment shown, spark head 22b includes a cup-shaped member 132a that may be configured to be acoustically reflective and an acoustically permeable cap member 136a. In this embodiment, cap member 136a is dome shaped to approximate the curved shape of an expanding wavefront that originates at the electrodes and to compress the skin when applied with moderate pressure. Cap member 136a can be coupled to cup-shaped member 132a with an O-ring or gasket (not shown, but similar to 140) and a retaining collar 144a. In the embodiment shown, cup-shaped member 132a has a cylindrical shape with a circular cross-section (e.g., with a diameter of 2 inches or less. In some embodiments, cup-shaped member can also include bayonet-style pins (not shown, but similar to 148, 152) configured to align with corresponding grooves in head 46a of probe 38a to lock the position of spark head 22b relative to the probe.

In the embodiment shown, conductors 160d, 160e, 160f extending through a rear portion (opposite outlet cap member 136a) of sidewall 132a, as shown. In this embodiment, central conductor 160b and peripheral conductors 160a, 160c can be molded into sidewall 120a such that grommets and the like are not necessary to seal the interface between the sidewall and the conductors. In the embodiment shown, a central conductor 160d serves as a ground to corresponding center electrodes 100d-1 and 100d-2, which are also in electrical communication with each other. Peripheral conductors 160e, 160f are in communication with peripheral electrodes 100e, 100f to generate sparks across the spark gap between electrodes 100d-1 and 100e, and between electrodes 100d-2 and 100f. It should be understood that while two spark gaps are shown, any number of spark gaps may be used, and may be limited only by the spacing and size of the spark gaps. For example, other embodiments include 3, 4, 5, 6, 7, 8, 9, 10, or even more spark gaps.

In the embodiment shown, central electrodes 100d-1 and 100d-2 are carried by, and may be unitary with, an elongated member 172 extending into chamber 124a toward cap member 136a from sidewall 120a. In this embodiment, member 172 is mounted to a hinge 176 (which is fixed relative to sidewall 120a) to permit the distal end of the member (adjacent electrodes 100d-1, 100d-2 to pivot back and forth between electrodes 100e and 100f, as indicated by arrows 180. In the embodiment shown, the distal portion of member 172 is biased toward electrode 100e by spring arms 184. In this embodiment, spring arms 184 are configured to position electrode 100d-1 at an initial spark gap distance from electrode 100e. Upon application of an electrical potential (e.g., via a pulse-generation system, as described elsewhere in this disclosure) across electrodes 100d-1 and 100e, a spark will arc between these two electrodes to release an electric pulse to vaporize liquid between these two electrodes. The expansion of vapor between these two electrodes drives member 172 and electrode 100d-2 downward toward electrode 100f. During the period of time in which member 172 travels downward, the pulse-generation system can re-charge and apply an electric potential between electrodes 100d-2 and 100f, such that when the distance between electrodes 100d-2 and 100f becomes small enough, a spark will arc between these two electrodes to release the electric pulse to vaporize liquid between these two electrodes. The expansion of vapor between electrodes 100d-2 and 100f then drives member 172 and electrode 100d-1 upward toward electrode 100e. During the period of time in which member 172 travels upward, the pulse-generation system can re-charge and apply an electric potential between electrodes 100d-1 and 100e, such that when the distance between electrodes 100d-1 and 100e becomes small enough, a spark will arc between these two electrodes to release the electric pulse and vaporize liquid between these two electrodes, causing the cycle to begin again. In this way, member 172 oscillates between electrodes 100e and 100f until the electric potential ceases to be applied to the electrodes.

The exposure to high-rate and high-energy electric pulses, especially in liquid, subjects the electrodes to rapid oxidation, erosion, and/or other deterioration that can vary the spark gap distance between electrodes if the electrodes are held in fixed positions (e.g., requiring electrodes to be replaced and/or adjusted). However, in the embodiment of FIG. 2B, the pivoting of member 172 and electrodes 100d-1, 100d-2 between electrodes 100e and 100f effectively adjusts the spark gap for each spark. In particular, the distance between electrodes at which current arcs between the electrodes is a function of electrode material and electric potential. As such, once the nearest surfaces (even if eroded) of adjacent electrodes (e.g., 100d-1 and 100e) reach a spark gap distance for a given embodiment, a spark is generated between the electrodes. As such, member 172 is configured to self-adjust the respective spark gaps between electrodes 100d-1 and 100e, and between electrodes 100d-2 and 100f.

Another example of an advantage of the present movable electrodes, as in FIG. 2B, is that multiple coils are not required as long as the electrodes are positioned such that only one pair of electrodes is within arcing distance at any given time, and such a single coil or coil system is configured to recharge in less time than it takes for member 172 to pivot from one electrode to the next. For example, in the embodiment of FIG. 2B, an electric potential may simultaneously be applied to electrodes 100e and 100f with electrodes 100d-1 and 100d-2 serving as a common ground, with the electric potential such that a spark will only arc between electrodes 100d-1 and 100e when member 172 is pivoted upward relative to horizontal (in the orientation shown), and will only arc between electrodes 100d-2 and 100f when member 172 is pivoted downward relative to horizontal. As such, as member 172 pivots upward and downward as described above, a single coil or coil system can be connected to both of peripheral electrodes 100e, 100f and alternately discharged through each of the peripheral electrodes. In such embodiments, the pulse rate can be adjusted by selecting the physical properties of member 172 and spring arms 184. For example, the properties (e.g., mass, stiffness, cross-sectional shape and area, length, and/or the like) of member 172 and the properties (e.g., spring constant, shape, length, and/or the like) of spring arms 184 can be varied to adjust a resonant frequency of the system, and thereby the pulse rate of the spark head or module 22b. Similarly, the viscosity of liquid 128a may be selected or adjusted (e.g., increased to reduce the speed of travel of arm 172, or decreased to increase the speed of travel of arm 172).

Another example of an advantage of the present movable electrodes, as in FIG. 2B, is that properties (e.g., shape, cross-sectional area, depth, and the like) of the electrodes can be configured to achieve a known effective or useful life for the spark head (e.g., one 30-minute treatment) such that spark head 22b is inoperative or of limited effectiveness after that designated useful life. Such a feature can be useful to ensure that the spark head is disposed of after a single treatment, such as, for example, to ensure that a new, sterile spark head is used for each patient or area treated to minimize potential cross-contamination between patients or areas treated.

FIG. 2C depicts an enlarged cutaway side view of a third embodiment of a removable spark head or module 22c. Spark head 22c is substantially similar to spark head 22b, except as noted below, and similar reference numerals are therefore used to designate structures of spark head 22c that are similar to corresponding structures of spark head 22b. The primary difference relative to spark head 22b is that spark head 22c includes a beam 172a that does not have a hinge, such that flexing of the beam itself provides the movement of electrodes 100d-1 and 100d-2 in the up and down directions indicated by arrows 180, as described above for spark head 22b. In this embodiment, the resonant frequency of spark head 22c is especially dependent on the physical properties (e.g., mass, stiffness, cross-sectional shape and area, length, and/or the like) of beam 172a. As described for spring arms 184 of spark head 22b, beam 172a is configured to be biased toward electrode 100e, as shown, such that electrode 100d-1 is initially positioned at an initial spark gap distance from electrode 100e. The function of spark head 22c is similar to the function of spark head 22b, with the exception that beam 172a itself bends and provides some resistance to movement such that hinge 176 and spring arms 184 are unnecessary.

In the embodiment shown, spark head 22b also includes liquid connectors or ports 188, 192 via which liquid can be circulated through spark chamber 124b. In the embodiment shown, a proximal end 196 of spark head 22b serves as a combined connection with two lumens for liquid (connectors or ports 188, 192) and two or more (e.g., three, as shown) electrical conductors (connectors 160d, 160e, 160f). In such embodiments, the combined connection of proximal end 196 can be coupled (directly or via a probe or handpiece) to a combined tether or cable having two liquid lumens (corresponding to connectors or ports 188, 192), and two or more electrical conductors (e.g., a first electrical conductor for connecting to connector 160d and a second electrical conductor for connecting to both peripheral connectors 160e, 160f). Such a combined tether or cable can couple the spark head (e.g., and a probe or handpiece to which the spark head is coupled) to a pulse-generation system having a liquid reservoir and pump such that the pump can circulate liquid between the reservoir and the spark chamber. In some embodiments, cap member 136a is omitted such that connectors or ports 188, 192 can permit liquid to be circulated through a larger chamber (e.g., 18a) of a handpiece to which the spark head is coupled. Likewise, a probe or handpiece to which spark head 22a is configured to be coupled can include electrical and liquid connectors corresponding to the respective electrical connectors (160d, 160e, 160f) and liquid connectors (188, 192) of the spark head such that the electrical and liquid connectors of the spark head are simultaneously connected to the respective electrical and liquid connectors of the probe or handpiece as the spark module is coupled to the handpiece (e.g., via pressing the spark head and probe together and/or a twisting or rotating the spark head relative probe).

In the present embodiments, a pulse rate of a few Hz to many KHz (e.g., up to 5 MHz) may be employed. Because the fatiguing event produced by a plurality of pulses, or shockwaves, is generally cumulative at higher pulse rates, treatment time may be significantly reduced by using many moderately-powered shockwaves in rapid succession rather than a few higher powered shockwaves spaced by long durations of rest. As noted above, at least some of the present embodiments (e.g., those with multiple spark gaps) enable electro-hydraulic generation of shockwaves at higher rates. For example, FIG. 3A depicts a timing diagram enlarged to show only two sequences of voltage pulses applied to the electrodes of the present embodiments, and FIG. 3B depicts a timing diagram showing a greater number of voltage pulses applied to the electrodes of the present embodiments.

In additional embodiments that are similar to any of spark modules 22a, 22b, 22c, a portion of the respective sidewall (120, 120a, 120b) may be omitted such that the respective spark chamber (124, 124a, 124b) is also omitted or left open such that liquid in a larger chamber (e.g., 18 or 18a) of a corresponding handpiece can freely circulate between the electrodes. In such embodiments, the spark chamber (e.g., sidewall 120, 120a, 120b can include liquid connectors or liquid may circulate through liquid ports that are independent of spark chamber (e.g., as depicted in FIG. 2).

The portion of pulse train or sequence 200 shown in FIG. 3A includes pulse groups 204 and 208 timed with a delay period 212 in between. Bursts or groups (e.g., 204, 208) may include as few as one or two, or as many as thousands, of pulses. In general, each group 204, 208 can include several voltage pulses that are applied to the electrodes to trigger an event (i.e., a spark across a spark gap). The duration of delay period 212 can be set to allow cooling of the electrodes across each spark gap and to allow recharging of the electronics. As used for the embodiments of this disclosure, pulse rate refers to the rate at which voltage pulse groups (each having one or more pulses) are applied to the electrodes; meaning that individual pulses within pulse groups having two or more pulses are applied at a greater frequency, as illustrated in FIGS. 3A-3B. Each of these pulse groups can be configured to generate one shock wave or a plurality of shock waves.

A series of events (sparks) initiated by a plurality of bursts or groups 204 and 208 delivered with the present systems and apparatuses can comprise a higher pulse rate (PR) that can reduce treatment time relative to lower pulse rates which may need to be applied over many minutes. Tattoos, for example, may encompass broad areas and therefore are time consuming to treat unless rapid cell destruction is achieved (e.g., with the higher pulse rates of the present disclosure). In contrast to the prior art systems noted above, the present embodiments can be configured to deliver shock waves at a relatively high pulse rate 216 of 10 to 5000 or more pulses per second (e.g., greater than any one of, or between any two of: 10 Hz, 30 Hz, 50 Hz, 1000 Hz, 10000 Hz, 1000000 Hz, 500000 Hz, and/or 5000000 Hz).

Figure 4:
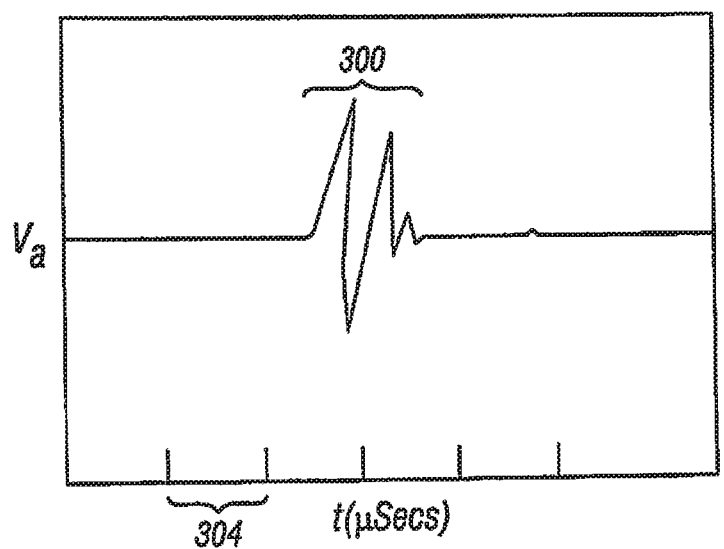
FIG. 4 depicts a waveform that can be emitted by system of FIG. 1 and/or the handheld probe of FIG. 2 into target tissue.

FIG. 4 depicts a waveform that can emitted by either of probes 38 or 38*a* into a volume of tissue, and that is of a form that can be useful for the elimination of tattoos. Pulse 300 is of a typical shaped for an impulse generated by the present EH spark heads at relatively high-voltage pulses. For example, pulse 300 has a rapid rise time, a short duration, and a ring down period. The units of vertical axis $V_a$ are arbitrary as may be displayed on an oscilloscope. The actual acoustic pulse amplitude may be as low as 50 µPa and as high as several MPa in various ones of the present embodiments, at least because cumulative energy delivery may be effective, as discussed above. The individual time periods 304 may be 100 nano-seconds each, which corresponds to short pulse lengths referred to in the art as "shockwave" pulses, owing to their sharpness and short rise and fall times. For example, a rise time of <30 nanoseconds is considered to be a shockwave for purposes of the present disclosure, the rapidity being particularly effective for producing relative arge presure-temporal pressure gradients across small, cellular-scaled structures in tissue (e.g., the dermis). Rapid compression and decompression of dermal structures containing tattoo "inks" which are actually particulate pigments, results in a fatiguing and destruction of the pigment-containing cells over time and is believed to be one underlying mechanism of the present methods, as described above. For example, agitation of tissue with such shock waves has been shown to be effective, when applied at high pulse rates within a relatively short time period, and at sufficient energy levels to produce a pigmented cell to rupture, with resulting liberation of entrapped particulates and subsequent dissemination of the pigment particles into the body, thereby reducing the appearance of the tattoo. It is believed to be necessary to have a short pulse waveform 300, which may be applied multiple times and preferably many hundreds to millions of times to an area to be treated to produce the fatigue needed for tattoo "ink" removal.

Figure 5:
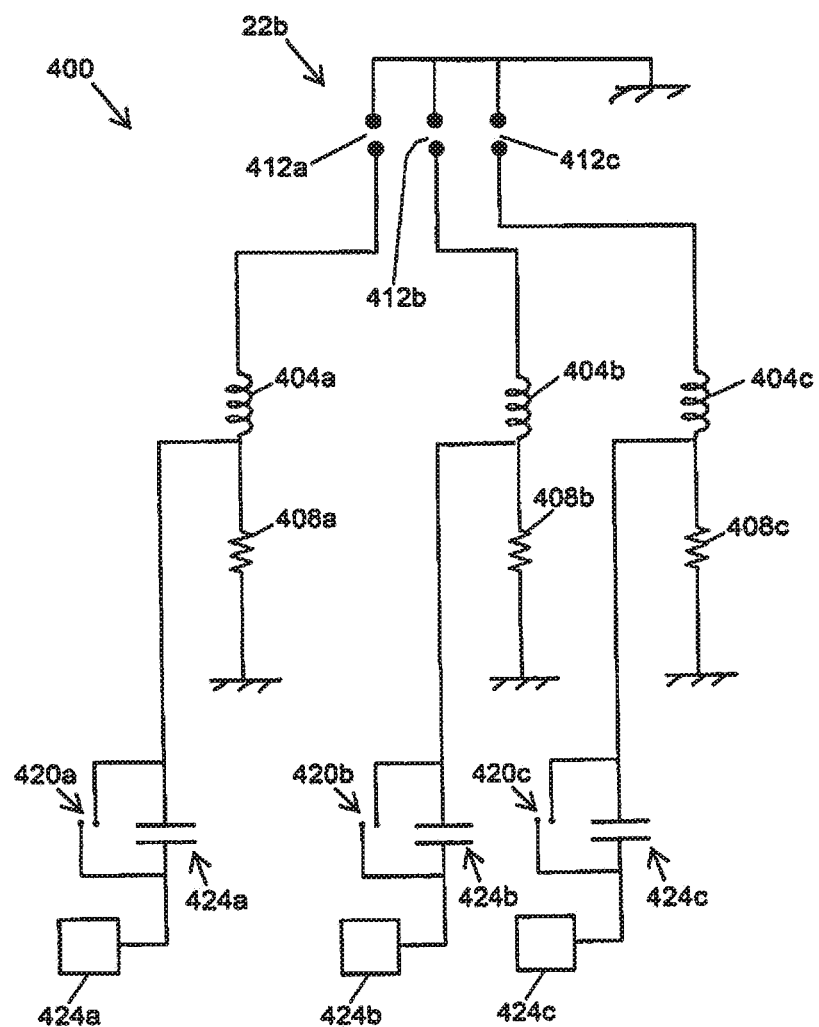
FIG. 5 depicts a schematic diagram of one embodiment of a multi-gap pulse-generation system for use in or with some embodiments of the present systems.

FIG. 5 depicts a schematic diagram of one embodiment 400 of a pulse-generation system for use in or with some embodiments of the present systems. In the embodiment shown, circuit 400 comprises a plurality of charge storage/discharge circuits each with a magnetic storage or induction type coil 404*a*, 404*b*, 404*c* (e.g., similar to those used in automotive ignition systems). As illustrated, each of coils 404*a*, 404*b*, 404*c*, may be grounded via a resistor 408*a*, 408*b*, 408*c* to limit the current permitted to flow through each coil, similar to certain aspects of automotive ignition systems. Resistors 408*a*, 408*b*, 408*c* can each comprise dedicated resistors, or the length and properties of the coil itself may be selected to provide a desired level of resistance. The use of components of the type used automotive ignition systems may reduce costs and improve safety relative to custom components. In the embodiment shown, circuit 400 includes a spark head 22*b* that is similar to spark head 22*a* with the exceptions that spark head 22*b* includes three spark gaps 412*a*, 412*b*, 412*c* instead of two, and that each of the three spark gaps is defined by a separate pair of electrodes rather than a common electrode (e.g., 100*a*) cooperating with multiple peripheral electrodes. It should be understood that the present circuits may be coupled to peripheral electrodes 100*b*, 100*c* of spark head 22*a* to generate sparks across the spark gaps defined with common electrode 22*a*, as shown in FIG. 2A. In the embodiment shown, each circuit is configured to function similarly. For example, coil 404*a* is configured to collect and store a current for a short duration such that, when the circuit is broken at switch 420*a*, the magnetic field of the coil collapses and generates a so-called electromotive force, or EMF, that results in a rapid discharge of capacitor 424*a* across spark gap 412*a*.

The RL or Resistor-Inductance time constant of coil 404*a*—which may be affected by factors such as the size and inductive reactance of the coil, the resistance of the coil windings, and other factors—generally corresponds to the time it takes to overcome the resistance of the wires of the coil and the time to build up the magnetic field of the coil, followed by a discharge which is controlled again by the time it takes for the magnetic field to collapse and the energy to be released through and overcome the resistance of the circuit. This RL time constant generally determines the maximum charge-discharge cycle rate of the coil. If the charge-discharge cycle is too fast, the available current in the coil may be too low and the resulting spark impulse weak. The use of multiple coils can overcome this limitation by firing multiple coils in rapid succession for each pulse group (e.g., 204, 208 as illustrated in FIG. 3A). For example, two coils can double the practical charge-discharge rate by doubling the (combined) current and resulting spark impulse, and three (as shown) can effectively triple the effective charge-discharge rate. When using multiple spark gaps, timing can be very important to proper generation of spark impulses and resulting liquid vaporization and shockwaves. As such, a controller (e.g., microcontroller, processer, FPGA, and/or the like) may be coupled to each of control points 428*a*, 428*b*, 428*c* to control the timing of the opening of switches 420*a*, 420*b*, 420*c* and resulting discharge of capacitors 424*a*, 424*b*, 424*c* and generation of shockwaves.

FIG. 6 depicts a block diagram of an embodiment 500 of a radio-frequency (RF) powered acoustic shockwave generation system. In the embodiment shown, system 500 comprises a nonlinear medium 504 (e.g., as in acoustic-delay chamber 58 or nonlinear member described above) that provides an acoustic path to from a transducer 512 to target tissue 508 to produce practical harmonic or acoustic energy (e.g., shockwaves). In the embodiment shown, transducer 512 is powered and controlled through bandpass filter and tuner 516, RF power amplifier 520, and control switch 524. The system is configured such that actuation of switch

524 activates a pulse generator 528 to produce timed RF pulses that drive amplifier 520 in a predetermined fashion. A typical driving waveform, for example, may comprise a sine wave burst (e.g., multiple sine waves in rapid succession). For example, in some embodiments, a typical burst may have a burst length of 10 milliseconds and comprise sine waves having a period duration of 0.1 (frequency of 100 MHz) to more than 2 microseconds (frequency of 50 kHz).

Embodiments of the present methods comprise positioning an embodiment of the present apparatuses (e.g., 10, 38, 38a, 500) adjacent to a region of a patient comprising target cells (e.g., tissue 74); and activating the spark generation (e.g., capacitive/inductive coil) system (e.g., 26, 400) to propagate shockwaves to the target cells. In some embodiments, the region is viewed through a window (e.g., 82, 82a) while positioning the apparatus and/or while the shockwaves are generated and delivered to the region. Some embodiments further comprise coupling a removable spark head or module (e.g., 22a, 22b) to a housing of the apparatus prior to activating the pulse-generation system.

Still other embodiments of the present methods for eliminating intradermal vacuoles formed when skin is treated with lasers. Such methods may comprise treating a section of tissue with a laser causing intradermal vacuoles to be formed, treating the vacuole containing tissue with an acoustic wave generator where the acoustic wave generator applies rapid pulsed acoustic waves to the skin at a frequency, pulse rate, and intensity to break up and disperse the intradermal vacuoles. These embodiments of the described system and method for dermal clearing of intradermal vacuoles utilize an acousto-mechanical effect to induce fragmentation and absorption of the vacuoles into the surrounding tissue. One embodiment of the method may include one or more of the following steps: coupling the acoustic wave generator to the tissue containing the vacuoles; and directing pulsed acoustic waves from the acoustic wave generator into the vacuole containing tissue. Directing pulsed acoustic waves into the tissue containing vacuoles will initiate an acousto-mechanical effect on the vacuoles resulting in the fragmentation of the vacuoles and the absorption of the vacuole contents into the surrounding tissue. This vacuole fragmentation and absorption leads to dermal clearing.

In some embodiments of the present methods and systems the acoustic wave generator may comprise an ultrasound generator or a shockwave generator. In some embodiments, the acoustic wave generator can be configured to produce pulsed acoustic waves with a frequency between about 700 KHz and about 100 MHz, including 750 KHz, 800 KHz, 850 KHz, 900 KHz, 950 KHz, 1 MHz, 2 MHz, 5 MHz, 10 MHz, 20 MHz, 30 MHz, 40 MHz, 50 MHz, 60 MHz, 70 MHz, 80 MHz, or 90 MHz.

In some embodiments, the acoustic wave generator can be configured to produce pulsed acoustic waves with a pulse duration between about 1 nanosecond and 1 microsecond, including 0.1 microseconds, 0.2 microseconds, 0.3 microseconds, 0.4 microseconds, 0.5 microseconds, 0.6 microseconds, 0.7 microseconds, 0.8 microseconds, or 0.9 microseconds.

In some embodiments, the acoustic wave generator can be configured to produce pulsed acoustic waves with a pulse rate between about 10 Hz and 1 KHz, including 50 Hz, 100 Hz, 200 Hz, 300 Hz, 400 Hz, 500 Hz, 600 Hz, 700 Hz, 800 Hz, or 900 Hz.

In some embodiments, the power of the described system is set so that the Mechanical Index is between about 0.15 and 1.9, including 0.2, 0.3, 0.4, 0.5, 0.6, 0.7, 0.8, 0.9, 1, 1.1, 1.2, 1.3, 1.4, 1.5, 1.6, 1.7, or 1.8. MI is calculated as shown in Equation (2):

$$MI = \frac{P[\text{MPa}]}{f[\text{MHz}]^{1/2}} \quad (2)$$

where P[MPA] is the amplitude of the acoustic wave pressure and f[MHz] is the ultrasound frequency. In some embodiments, the power of the described system is set so that the peak pressure output is between 0.8 MPa and 20 MPa.

In an embodiment, the acoustic wave is generated from a rapid pulse electrohydraulic (EH) shockwave generator or a megasonic wave generator. In some embodiments, the disclosed system for electrohydraulic generation of shockwaves comprises: a housing defining a chamber and a shockwave outlet; a liquid disposed in the chamber; a plurality of electrodes (e.g., in spark head or module) configured to be disposed in the chamber to define one or more spark gaps; and a pulse-generation system configured to apply voltage pulses to the electrodes at a rate of between about 10 Hz and about 5 MHz. In one embodiment, the pulse generation system is configured to apply the voltage pulses directly to the electrodes.

In one embodiment, the megasonic wave generator is configured to produce pulsed acoustic waves with a frequency between 1.0 and 9.0 MHz; a pulse duration between 1 nanosecond and 1 microsecond; a pulse rate between 50 Hz and 500 Hz; and a power set so that the Mechanical Index (MI) is between 0.15 and 1.9.

Other embodiments of the present methods for rapid laser-based tattoo removal comprise the repeated steps of treating the tattooed skin with a laser then treating the tattoo site with an acoustic wave generator. The acoustic wave generator applies rapid pulsed acoustic waves to the skin at a frequency, pulse rate, and intensity to breakup and disperse intradermal vacuoles. These embodiments allow for and enable repeated laser treatments over the same treatment area in quick succession, something that was not possible in prior art methods.

In certain embodiments, the laser used by the described pulsed acoustic wave post-laser dermal clearing system and method may be any high powered dermal laser system. More specifically, in some embodiments, the laser used a Q Switched (QS) laser and/or a pico-second laser system.

Other embodiments use the pulsed acoustic wave dermal clearing system and method in conjunction with topical and intradermal dermal clearing agents such as perfluorodecalin, glycerol, etc.

Experimental Results

Experiments were conducted on Gottingen Minipigs to observe effects of rapid pulsed acoustic waves generated by an acoustic wave generator to laser treated skin intended to eliminate intradermal vacuoles. A study was undertaken to demonstrate the elimination of "whitening" caused by intradermal vacuoles as a result of laser treatment using a rapid pulse electrohydraulic (EH) shockwave generator.

While the high frequency shock waves generated by certain embodiments of the present disclosure and the controlled and predictable manner of generating them have many applications, certain embodiments of the present disclosure and the generated shock waves are particularly useful in therapeutic applications. Specifically, in eliminating dermal vacuoles of a patient formed from laser skin treatment.

Figure 7A:
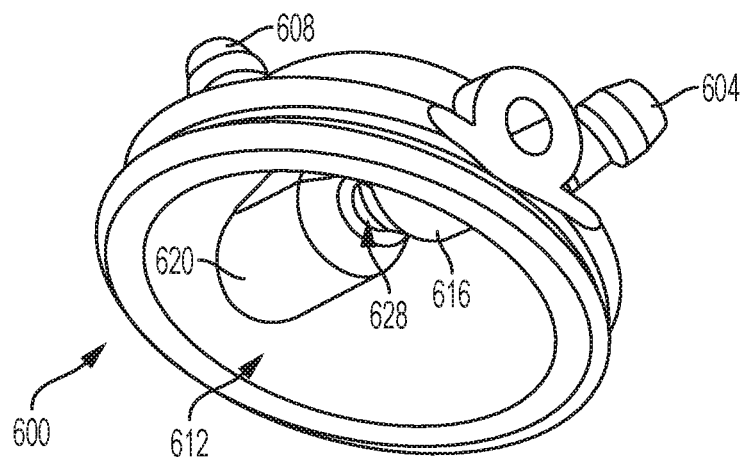
FIGS. 7A-7B depict perspective and cross-sectional views of a first prototyped spark chamber housing.
Figure 7B:
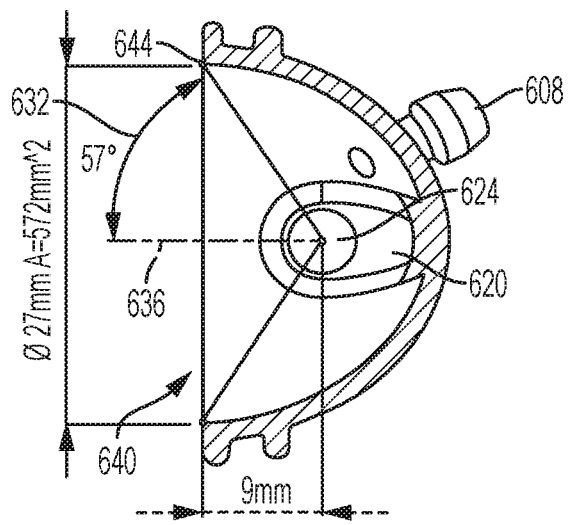
Figure 8:
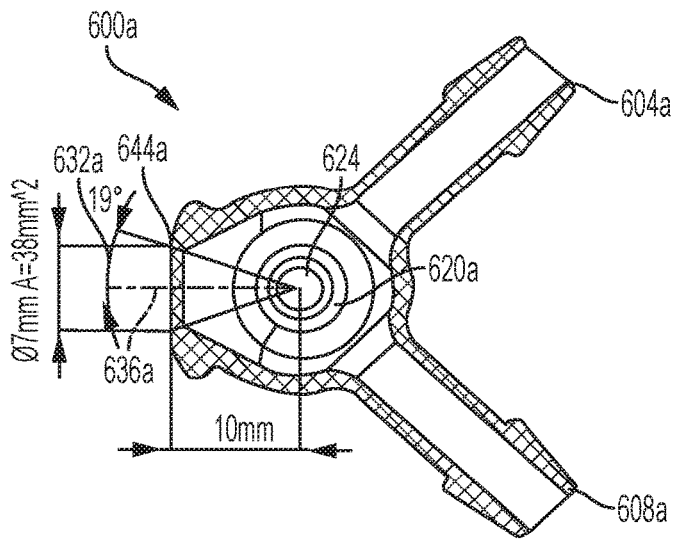
FIG. 8 depicts a cross-sectional view of a second prototyped embodiment of spark chamber housing.

FIGS. 7A-7B and 8 depict two different prototype spark chamber housings. The embodiment of FIGS. 7A-7B depict a first embodiment 600 of a spark chamber housing that was used in the described experiments. Housing 600 is similar in some respects to the portion of housing 14a that defines head 46a of probe 38a. For example, housing 600 includes fittings 604, 608 to permit liquid to be circulated through spark chamber 612. In the embodiment shown, housing 600 includes electrode supports 616 and 620 through which electrodes 624 can be inserted to define a spark gap 628 (e.g., of 0.127 millimeters or 0.005 inches in the experiments described below). However, housing 600 has an elliptical inner surface shaped to reflect the shockwaves that initially travel backwards from the spark gap into the wall. Doing so has the advantage of producing, for each shockwave generated at the spark gap, a first or primary shockwave that propagates from the spark gap to outlet 640, followed by a secondary shock wave that propagates first to the elliptical inner wall and is then reflected back to outlet 640.

In this embodiment, supports 616 and 620 are not aligned with (rotated approximately 30 degrees around chamber 612 relative to) fittings 604, 608. In the embodiment shown, housing 600 has a hemispherical shape and electrodes 624 are positioned such that an angle 632 between a central axis 636 through the center of shockwave outlet 640 and a perimeter 644 of chamber 612 is about 57 degrees. Other embodiments can be configured to limit this angular sweep and thereby direct the sound waves and/or shockwaves through a smaller outlet. For example, FIG. 8 depicts a cross-sectional view of a second embodiment 600a of a spark chamber housing. Housing 600a is similar to housing 600, with the exception that fittings 604a, 608a are rotated 90 degrees relative to supports 616a, 620a. Housing 600a also differs in that chamber 612a includes a hemispherical rear or proximal portion and a frusto-conical forward or distal portion. In this embodiment, electrodes 624a are positioned such that such that an angle 632a between a central axis 636a through the center of shockwave outlet 640a and a perimeter 644a of chamber 612a is about 19 degrees.

Figure 9:
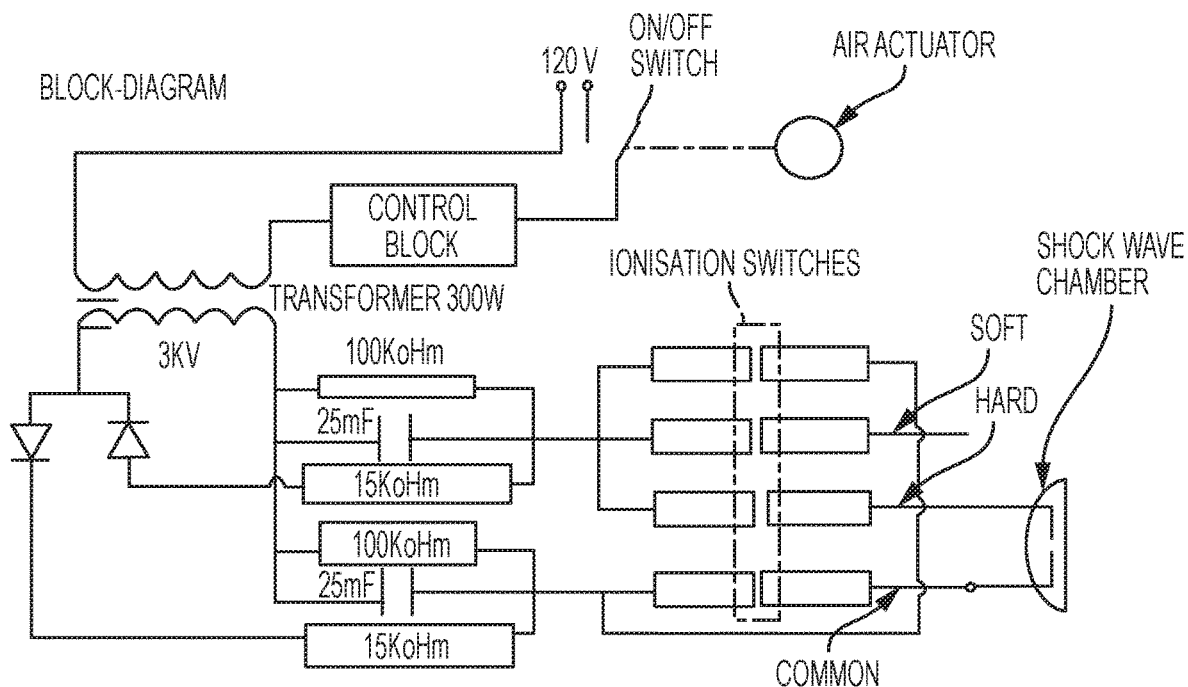
FIG. 9 depicts a schematic diagram of an electric circuit for a prototyped pulse-generation system.

FIG. 9 depicts a schematic diagram of an electric circuit for a prototyped pulse-generation system used with the spark chamber housing of FIGS. 7A-7B in the present experimental procedures. The schematic includes symbols known in the art, and is configured to achieve pulse-generation functionality similar to that described above. The depicted circuit is capable of operating in the relaxation discharge mode with embodiments of the present shockwave heads (e.g., 46, 46a, etc.). As shown, the circuit comprises a 110V alternating current (AC) power source, an on-off switch, a timer ("control block"), a step-up transformer that has a 3 kV or 3000V secondary voltage. The secondary AC voltage is rectified by a pair of high voltage rectifiers in full wave configuration. These rectifiers charge a pair of oppositely polarized 25 mF capacitors that are each protected by a pair of resistors (100 kΩ and 25 kΩ) in parallel, all of which together temporarily store the high-voltage energy. When the impedance of the shockwave chamber is low and the voltage charge is high, a discharge begins, aided by ionization switches, which are large spark gaps that conduct when the threshold voltage is achieved. A positive and a negative voltage flows to each of the electrodes so the potential between the electrodes can be up to about 6 kV or 6000 V. The resulting spark between the electrodes results in vaporization of a portion of the liquid into a rapidly-expanding gas bubble, which generates a shock wave. During the spark, the capacitors discharge and become ready for recharge by the transformer and rectifiers. In the experiments described below, the discharge was about 30 Hz, regulated only by the natural rate of charge and discharge—hence the term "relaxation oscillation." In other embodiments, the discharge rate can be as higher (e.g., as high as 100 Hz, such as for the multi-gap configuration of FIG. 5.

Further embodiments of the present EH shockwave generating systems and apparatuses are depicted in FIGS. 11-13C. Probe 38b is similar in some respects to probes 38 and 38a, and the differences are therefore primarily described here. In this embodiment, probe 38b comprises: a housing 14b defining a chamber 18b and a shockwave outlet 20b; a liquid (54) disposed in chamber 18b; a plurality of electrodes (e.g., in spark head or module 22d) configured to be disposed in the chamber to define one or more spark gaps; and is configured to be coupled to a pulse-generation system 26 configured to apply voltage pulses to the electrodes at a rate of between 10 Hz and 5 MHz.

In the embodiment shown, spark head 22d includes a sidewall or body 120d and a plurality of electrodes 100g that define a spark gap. In this embodiment, probe 38b is configured to permit liquid to be circulated through chamber 18b via liquid connectors or ports 112b and 116b, one of which is coupled to spark head 22d and the other of which is coupled to housing 14b, as shown. In this embodiment, housing 14b is configured to receive spark head 22d, as shown, such that housing 14b and housing 120d cooperate to define chamber 18b (e.g., such that spark head 22d and housing 14b include a complementary parabolic surfaces that cooperate to define the chamber). In this embodiment, housing 14b and spark head 22d includes acoustically-reflective liners 700, 704 that cover their respective surfaces that cooperate to define chamber 18b. In this embodiment, housing 120d of spark head 22d includes a channel 188b (e.g., along a central longitudinal axis of spark head 22d) extending between liquid connector 112b and chamber 18b and aligned with the spark gap between electrodes 100g such that circulating water will flow in close proximity and/or through the spark gap. In the embodiment shown, housing 14b includes a channel 192b extending between connection 116b and chamber 18b. In this embodiment, housing 120d includes a groove 708 configured to receive a resilient gasket or O-ring 140a to seal the interface between spark head 22d and housing 14b, and housing 14b includes a groove 712 configured to receive a resilient gasket or O-ring 140b to seal the interface between housing 14b and cap member 136b when cap member 136b is secured to housing 14b by ring 716 and retaining collar 144b.

In the embodiment shown, electrodes 100g each includes a flat bar portion 724 and a perpendicular cylindrical portion 728 (e.g., comprising tungsten for durability) in electrical communication (e.g., unitary with) bar portion 724 such that cylindrical portion 728 can extend through a corresponding opening 732 in spark head 22d into chamber 18b, as shown. In some embodiments, part of the sides of cylindrical portion 728 can be covered with an electrically insulative and/or resilient material (e.g., shrink wrap) such as, for example, to seal the interface between portion 728 and housing 120b. In this embodiment, housing 120b also includes longitudinal grooves 732 configured to receive bar portions 724 of electrodes 100g. In the embodiment shown, housing 38g also includes set screws 736 positioned align with cylindrical portions 732 of electrodes 100g when spark head 22d is disposed in housing 38g, such that set screws 736 can be tightened to press cylindrical portions 736 inward to adjust the spark gap between the cylindrical portions of electrodes 100g. In some embodiments, spark head 22d is permanently adhered to housing 38b; however, in other embodiments, spark head 22d may be removable from housing 38b such as, for example, to permit replacement of electrodes 100g individually or as part of a new or replacement spark head 22d.

Figure 14:
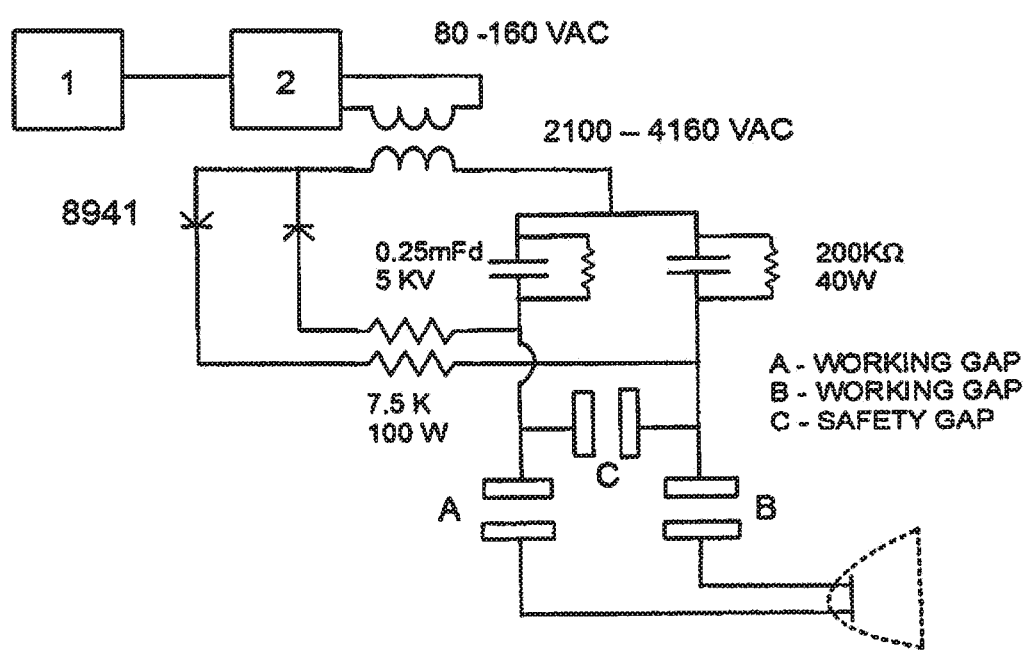
FIG. 14 depicts a schematic diagram of a second embodiment of an electric circuit for a prototyped pulse-generation system.

FIG. 14 depicts a schematic diagram of a second embodiment of an electric circuit for a prototyped pulse-generation system. The circuit of FIG. 14 is substantially similar to the circuit of FIG. 9 with the primary exception that the circuit of FIG. 14 includes an arrangement of triggered spark gaps instead of ionization switches, and includes certain components with different properties than corresponding components in the circuit of FIG. 9 (e.g., 200 kΩ resistors instead of 100 kΩ resistors). In the circuit of FIG. 14, block "1" corresponds to a primary controller (e.g., processor) and block "2" corresponds to a voltage timer controller (e.g., oscillator), both of which may be combined in a single unit in some embodiments.

Figure 15:
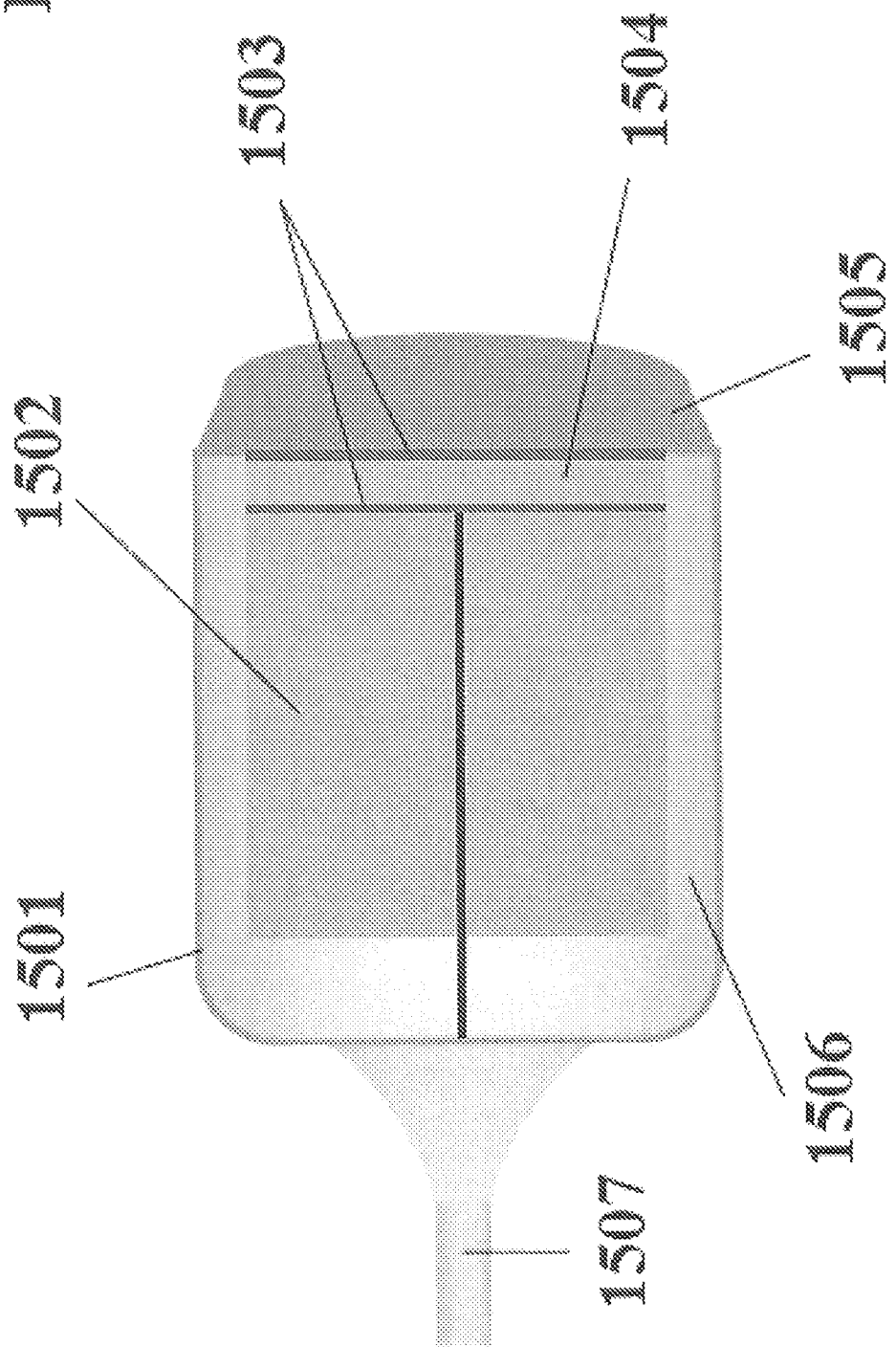
FIG. 15 depicts a cross-sectional view of an ultrasound generator probe.

FIG. 15 depicts a cross-section of an embodiment of an ultrasound generator probe. In one embodiment, the power cable 1507 attaches to the proximal end of the metal outer casing 1501. The casing 1501 may contain the acoustic insulator 1506, the backing block 1502, piezoelectric crystal 1504, and electrodes 1503 which apply an alternating potential difference to the crystal 1504. In an embodiment, the distal end of the casing 1501 is capped by a plastic "nose" 1505.

A. Tattoos

Tattoos are essentially phagocytosing cells such as fibroblast cells, macrophages, and the like that contain agglomerates of ink particles. Because the captured ink particles are denser than the biological structures of the cells, tattoos or cells containing ink particles have a large difference in elasticity in its structure. When subject to shock waves, the cells containing ink particles are subject to greater mechanical strain as compared to other cells that do not contain dense particles. Shock waves can be configured to be delivered at an optimal frequency and amplitude to accelerate the ink particles sufficiently to rupture the particular cells while leaving intact fibroblast cells that do not have the particular elasticity difference. The details of tattoos and biological process of removal of released from cells are discussed further below.

Tattoo inks and dyes were historically derived from substances found in nature and generally include a heterogeneous suspension of pigmented particles and other impurities. One example is India ink, which includes a suspension of carbon particles in a liquid such as water. Tattoos are generally produced by applying tattoo ink into the dermis, where the ink generally remains substantially permanently. This technique introduces the pigment suspension through the skin by an alternating pressure-suction action caused by the elasticity of the skin in combination with the up-and-down movement of a tattoo needle. Water and other carriers for the pigment introduced into the skin diffuse through the tissues and are absorbed. For the most part, 20%-50% of the pigment is disseminated into the body. However, the remaining portion of the insoluble pigment particles are deposited in the dermis where placed. In tattooed skin, pigment particles generally are phagocytized by cells resulting in pigment agglomerates in the cytoplasm of the cells (i.e., in the membrane-bound structures known as secondary lysosomes). Resulting pigment agglomerates ("particle agglomerates") may range up to a few micrometers in diameter. Once the skin has healed, the pigment particles remain in the interstitial space of the skin tissue within the cells. Tattoo inks generally resist elimination due to the cells immobility due to the relatively large amount of insoluble pigment particles in the cells. A tattoo may fade over time, but will generally remain through the life of the tattooed person.

Tattoo inks typically comprise aluminum (87% of the pigments), oxygen (73% of the pigments), titanium (67% of the pigments), and carbon (67% of the pigments). The relative contributions of elements to the tattoo ink compositions were highly variable between different compounds. At least one study has determined the particle size for three commercial tattoo inks as shown in Table 1:

TABLE 1

| Tattoo Pigment Particle Size | | |
|---|---|---|
| Color | Mean Diameter | Std deviation |
| Viper Red | 341 nm | 189 nm |
| Agent Orange | 228 nm | 108 nm |
| Hello yellow | 287 nm | 153 nm |

B. Tattoo Removal

In conventional tattooing (decorative, cosmetic, and reconstructive), once the pigment or dye has been administered into the dermis to form a tattoo, the pigment or dye generally remains permanently in place, as discussed above.

Despite the general permanency of tattoos, individuals may wish to change will remove tattoos for a variety of reasons. For example, over time people may have a change of heart (or mind), and may desire to remove or change the design of a decorative tattoo. By way of another example, an individual with cosmetic tattooing, such as eyeliners, eyebrows, or lip coloring, may wish to change the color or area tattooed as fashion changes. Unfortunately, there is currently no simple and successful way to remove tattoos. Currently, methods of removing traditional tattoos (e.g., pigment-containing skin) may include salabrasion, cryosurgery, surgical excision, and CO2-laser. These methods may require invasive procedures associated with potential complications, such as infections, and usually results in conspicuous scarring. More recently, the use of Q-switched lasers has gained wide acceptance for the removal of tattoos. By restricting pulse duration, ink particles generally reach very high temperatures resulting in the destruction of the tattoo ink pigment-containing cells with relatively minimal damage to adjacent normal skin. This significantly decreases the scarring that often results after nonselective tattoo removal methods, such as dermabrasion or treatment with carbon dioxide laser. The mechanisms of tattoo removal by Q-switch laser radiation may still be poorly understood. It is thought that Q-switch laser allow for more specific removal of tattoos by the mechanisms of selective photothermolysis and thermokinetic selectivity. Specifically, it is thought that the pigment particles in cells are able to absorb the laser light causing heating of the particles resulting thermal destruction of the cells containing said particles. The destruction of these cells results in the release of particles which can then be removed from the tissue through normal absorptive processes.

While the Q-switch laser may be better than some alternatives for the removal of tattoos, it is not perfect. Some tattoos are resistant to all laser therapies despite the predicted high particle temperatures achieved through selective photothermolysis. Reasons cited for failure of some tattoos to clear include the absorption spectrum of the pigment, the depth of pigment, and structural properties of some inks. Adverse effects following laser tattoo treatment with the Q-switched ruby laser may include textural changes, scarring, and/or pigmentary alteration. Transient hypopigmentation and textural changes have been reported in up to 50 and 12%, respectively, of patients treated with the Q-switched alexandrite laser. Hyperpigmentation and textural changes are infrequent adverse effects of the Q-switched Nd:YAG laser and the incidence of hypopigmentary changes are generally lower than with the ruby laser. The development of localized and generalized allergic reactions is also impossible (even if unusual) complication of tattoo removal with the Q-switched ruby and Nd:YAG lasers. Additionally, laser treatment may be painful, such that use of a local injection with lidocaine or topical anesthesia cream typically is used prior to laser treatment. Finally, laser removal generally requires multiple treatment sessions (e.g., 5 to 20) and may require expensive equipment for maximal elimination. Typically, since many wavelengths are needed to treat multicolored tattoos, not one laser system can be used alone to remove all the available inks and combination of inks. Even with multiple treatments, laser therapy may only be able to eliminate 50-70% of the tattoo pigment, resulting in a residual smudge.

In investigating the effects of conventional laser tattoo removal, experiments showed that the initial QS laser treatment to both the control and test black tattoo sites resulted in a sharp snap sound when the tattoo sites were pulsed with the laser. Additionally, each laser pulse to an untreated tattoo area resulted in immediate "whitening" on the black tattoo site.

A Gottingen Minipig, having a mass of roughly 30 Kg, that was previously tattooed was anesthetized. A control site and a test site consisting of black tattoos were treated with a QS laser (1054 wavelength, 5 Hz, 5 mm spot size, 1.1 W output). Immediately following the laser treatment, the test site was treated with a rapid pulse electrohydraulic shockwave generator (as described in US2014/021746) for two minutes. The EH shockwave generator produced planar shockwaves having peak pressures between 2 MPa and 3.5 MPa at a pulse rate of 50 Hz. Following the rapid pulse EH shockwave treatment, both the control site and the test site were once against treated with the QS laser. The test site was then treated again with the rapid pulse EH shockwave generator. This treatment protocol was repeated once again so that the control site and the test site had been treated for a total of three (3) times with the QS laser. At the test site each QS laser treatment was followed by the rapid pulse EH shockwave treatment. Following all treatments, each tattoo was biopsied for histological examination.

Methods

For the test site, applying the EH shockwave treatment for two (2) minutes resulted in a return of the tattoo color and a loss of the "whitening." During this period of time there was no observed dissipation of the "whitening" of the control site. Furthermore, when the second round of laser pulses were applied to the EH generator treated test site, the laser pulses resulted in sharp snap sounds and the immediate and substantial "whitening" of the black tattoo site once again. Applying the second round of laser pulses to the already "whitened" control site resulted in a dull sound with only slight additional "whitening." The results of the third round of laser treatment with EH shockwaves were similar to the first two rounds.

The visual and aural findings provide evidence that the acoustic waves were able to eliminate the intradermal vacuoles. This provided the ability to repeat laser treatments at the tattoo site. Visually, the elimination of the dermal "whitening" with the return of the color at the black tattoo site indicates that the intradermal vacuoles, which result in ineffective repeat laser performance, was eliminated.

For the EH treated sites, laser pulses to the previously treated test tattoo sites resulted once again in the generation of a sharp snap sound. This indicates that the laser light was once again able to reach black tattoo pigment resulting in the snapping sound caused by a micro-explosion from the superheated pigment. In contrast, laser pulses to the previously treated control tattoo sites resulted in only dull sounds. This indicates that the laser light was limited in its ability to reach black tattoo pigment due to laser attenuation resulting from light scattering by the dermal vacuoles, thereby limiting the laser's ability to cause the desired pigment microexplosions.

Examples of laser skin treatments that produce epidermal and/or intradermal vacuoles include laser tattoo removal, laser skin resurfacing, laser removal of birthmarks, laser removal of skin lesions, laser hair transplants, laser scar removal, laser-assisted hair reduction, laser removal of vascular lesions, laser lip lightening, or laser treatment of melasma. These are merely non-limiting exemplary treatment that can be supplemented or assisted by rupturing or destruction of vacuoles caused by laser skin treatment. In some embodiments, destruction or dispersion of the vacuoles caused by laser skin treatment may be caused by non-thermal cell membrane degradation of the specific cells secondary to nonlinear processes accompanying propagation of high frequency shock waves, as discussed above.

Some general embodiments of the present methods comprise: delivering a plurality generated (e.g., via one or more of the present apparatuses) shock waves to at least one dermal vacuole comprising at least one region of heterogeneity until the at least one dermal vacuole ruptures or disperses. In some embodiments, the shock waves are delivered for no more than 30 minutes in a 24-hour period. In some embodiments, the shock waves are delivered for no more than 20 minutes in a 24-hour period. In some embodiments, between 200 and 5000 shockwaves are delivered in between 30 seconds and 20 minutes at each of a plurality of positions of a shockwave outlet.

Figure 16:
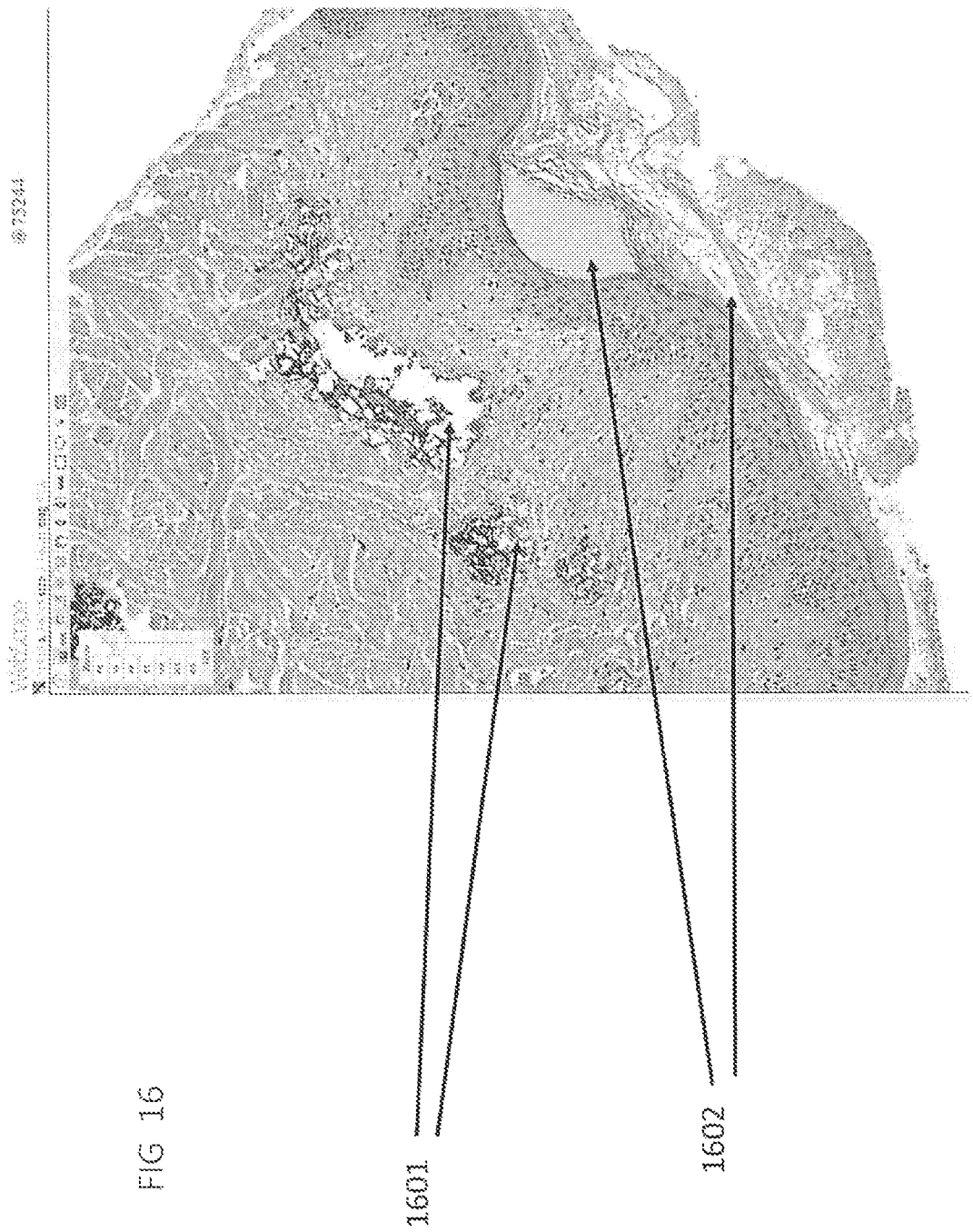
FIG. 16 depicts a histological image of skin containing blue tattoo pigment that has had a single laser treatment.

FIG. 16 provides a histological image of skin containing blue tattoo pigment that has had a single laser treatment. As can be seen from the image, there is considerable vacuole formation 1602 at the epidermis-dermis border and adjacent to the tattoo pigment particle agglomerations 1601.

Figure 17:
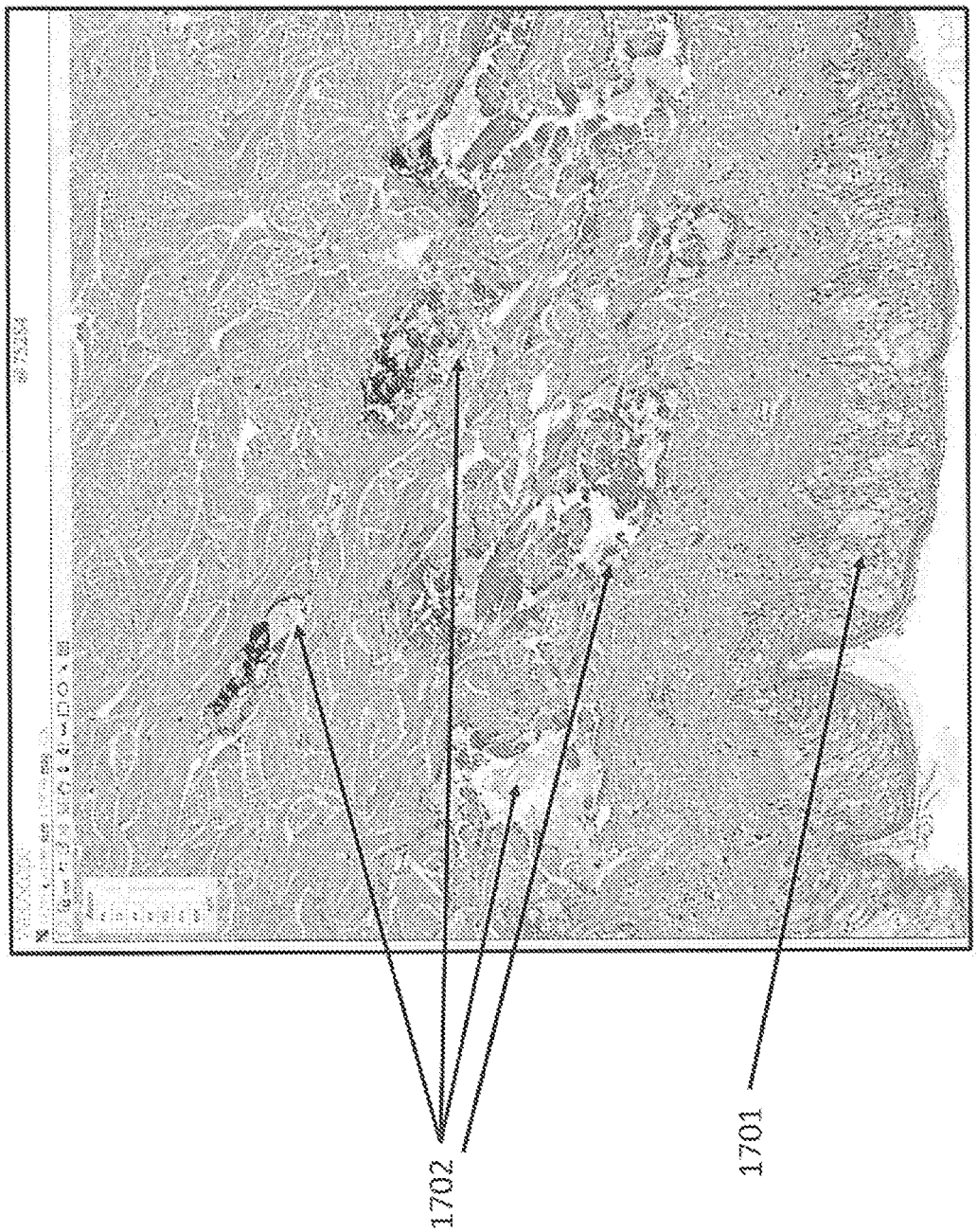
FIG. 17 depicts a histological image of skin containing black tattoo pigment that has had three rounds of laser treatment (application of the laser three times).
Figure 18:
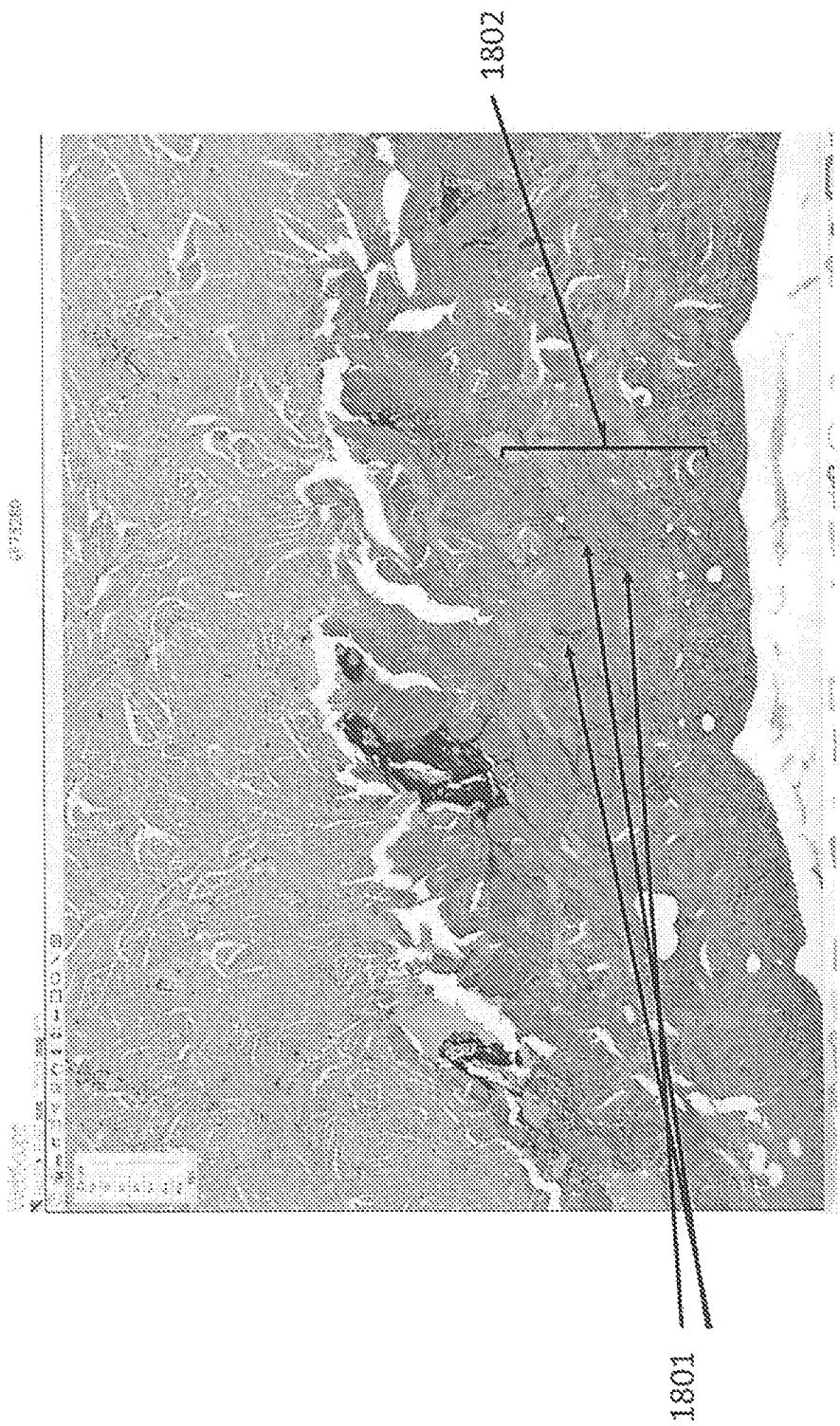
FIG. 18 depicts a histological image of skin containing black tattoo pigment that has been treated with three applications of laser treatment followed by rapid pulse shockwaves.

FIGS. 17 and 18 provide histological images for biopsies taken from the control site and test site respectively after the completion of the study. More specifically, FIG. 17 depicts the control black tattoo site treated three times with laser treatment only. As can be seen from FIG. 17, the control site had significant amount of microbubbles both at the epidermal-dermal boundary and around the black tattoo pigment clusters. Under current understanding, the vacuoles at the epidermal-dermal boundary 1701 are the major source, visually, of the "whitening" seen following laser treatment. However, more importantly, the vacuoles that are around the pigment particles 1702 within the dermis are likely another source of laser ineffectiveness with repeated laser treatments.

FIG. 18 depicts the test black tattoo site treated three times with laser treatment with accompanying rapid pulse shockwave treatment. FIG. 18 shows there is significant evidence of bleached pigment 1801 indicating that the black pigment particles had been successfully treated by the laser. Additionally, FIG. 18 depicts a portion of tissue that contains minimal vacuoles 1802 when compared to the corresponding tissue from the control site in FIG. 17. This result provides solid evidence that "whitening" from a laser treated tattoo site can be minimized allowing repeated treatment of a tattoo site in a single-session.

Figure 10:
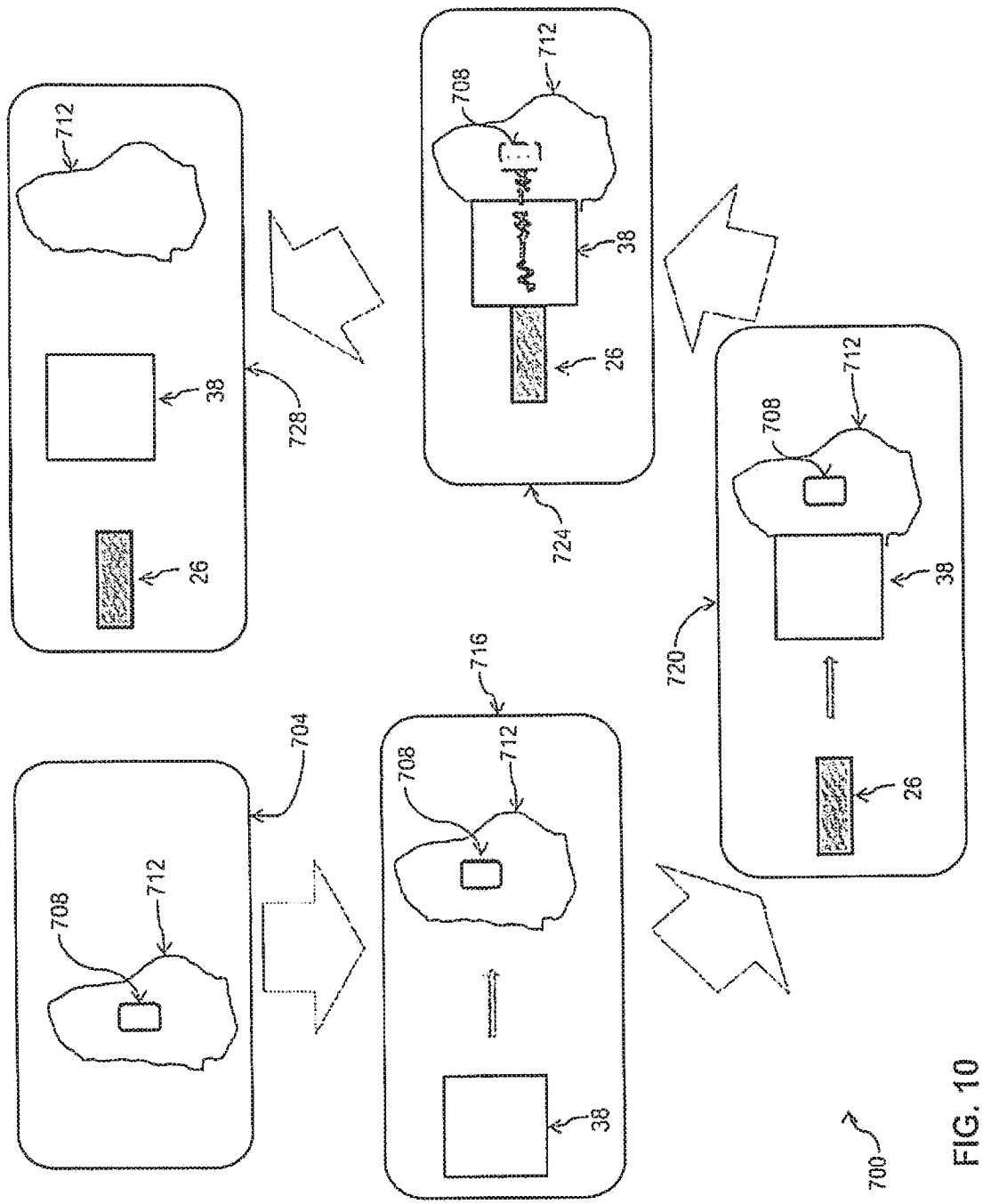
FIG. 10 depicts a conceptual flowchart of one embodiment of the present methods.
Figure 11:
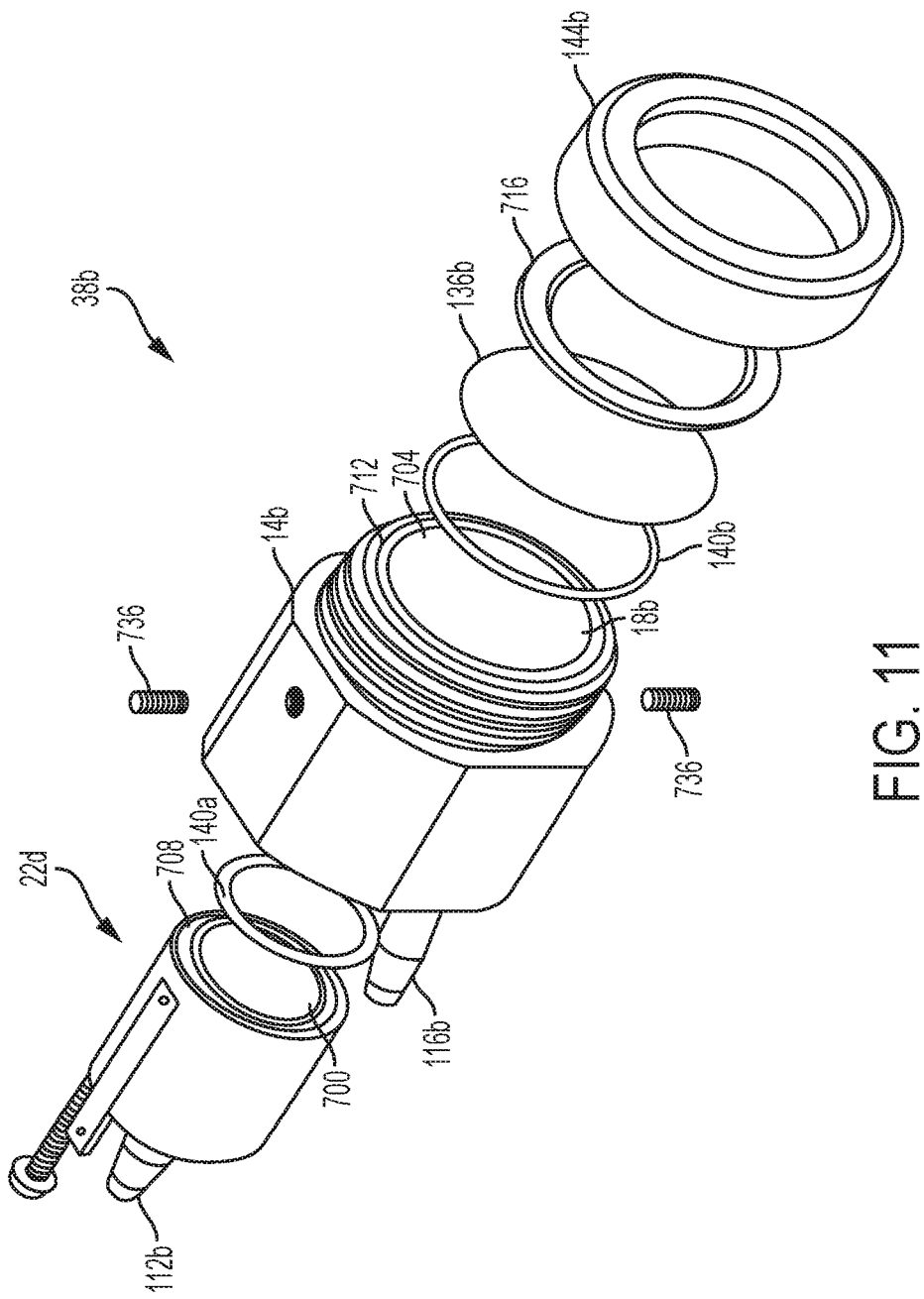
FIG. 11 depicts an exploded perspective view of a further prototyped embodiment of the present probes having a spark head or module.
Figures 12A, 12B:
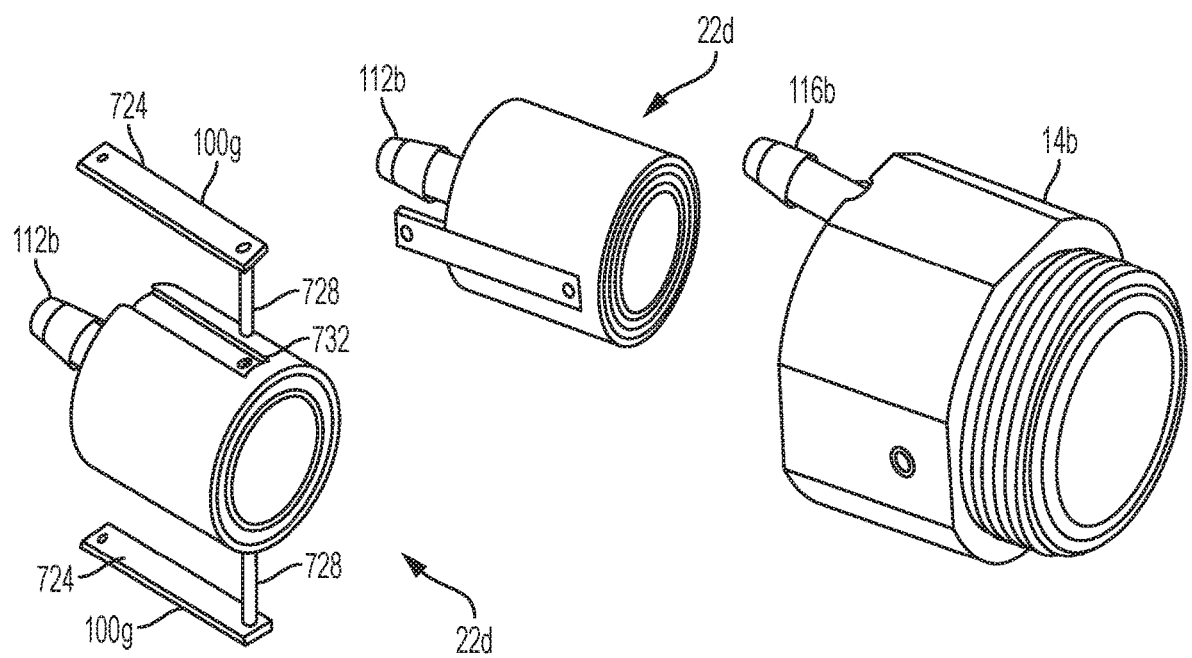
FIGS. 12A and 12B depict parts of the assembly of the probe of FIG. 11.
Figure 13A:
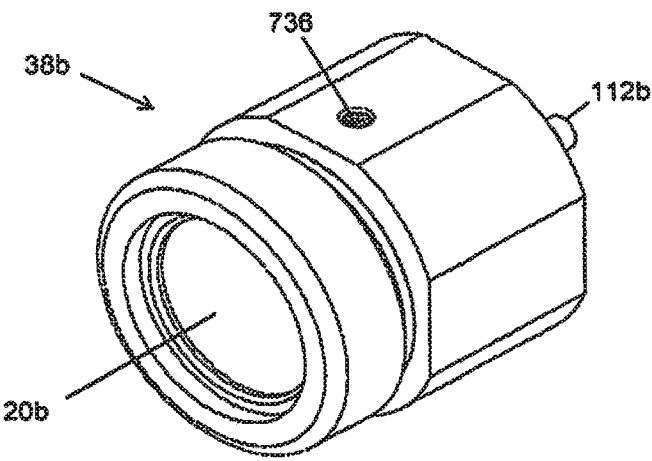
FIGS. 13A and 13B depict perspective and side cross-sectional views, respectively, of the probe of FIG. 11.
Figure 13B:
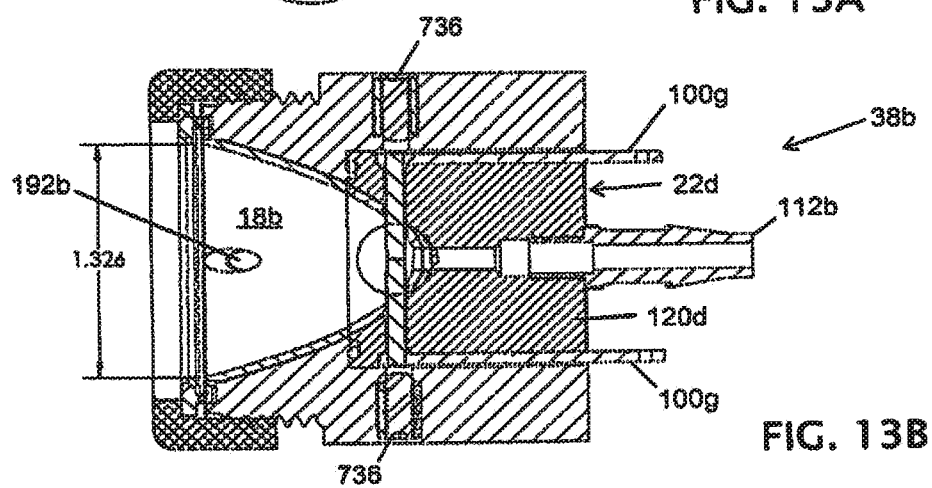
Figure 13C:
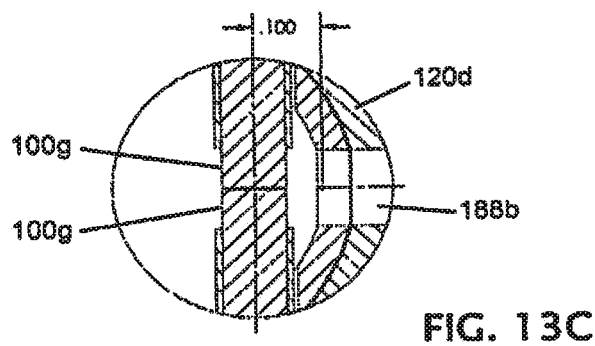
FIG. 13C depicts an enlarged side cross-sectional view of a spark gap of the probe of FIG. 11.

FIG. 10 illustrates one embodiment of a method 700 of using apparatus 10 to direct shockwaves to target tissue. In the embodiment shown, method 700 comprises a step 704 in which target cells 708 of a patient's tissue 712 are identified for treatment. For example, tissue 712 can comprise skin tissue, and target cells 708 can comprise cells containing tattoo pigment and/or vacuoles within or near skin tissue. In the embodiment shown, method 700 also comprises a step 716 in which a probe or handpiece 38 is disposed adjacent tissue 712, such that shockwaves originating in probe 38 can be directed toward the target cells 708. In the embodiment shown, method 700 also comprises a step 720 in which a pulse-generation system 26 is coupled to probe 38. In the embodiment shown, method 700 also comprises a step 724 in which pulse-generation system 26 is activated to generate sparks across electrodes within probe 38 to generate shockwaves in probe 38 for delivery to target cells 708, as shown. In the embodiment shown, method 700 also comprises an optional step 728 in which pulse-generation system 26 is de-coupled from probe 38, and probe 38 is removed from or moved relative to tissue 712. In the embodiment shown, target cells 708 are omitted from step 728, representing their destruction. Other embodiments of the present methods may comprise some or all of the steps illustrated in FIG. 10.

C. Use of Acoustic Waves on Intradermal Vacuoles

Acoustic waves have been used previously for the destruction of contrast microbubbles used for medical imaging and drug delivery (as shown in Chatterjee D., et al, *Ultrasound-medicated destruction of contrast microbubbles used for medical imaging and drug delivery*, PHYSICS OF FLUID 17, 100603 (2005)). The destruction of these bubbles is typically a result of rupturing the encapsulating membrane which permits the diffusion of gas into the body.

These contrast microbubbles, as well as others in the prior art, are typically less than 2 micrometers in diameter and formed by encapsulating a liquid or gas in a stabilizing layer of surface-active materials. As disclosed in the prior art, smaller bubbles with a larger surface-to-volume ration seem to be less stable because stronger diffusion. Despite the small sizes of the contrast microbubbles, the significant destruction of the bubbles takes 4-10 minutes depending on the acoustic pressures used.

Figure 19:
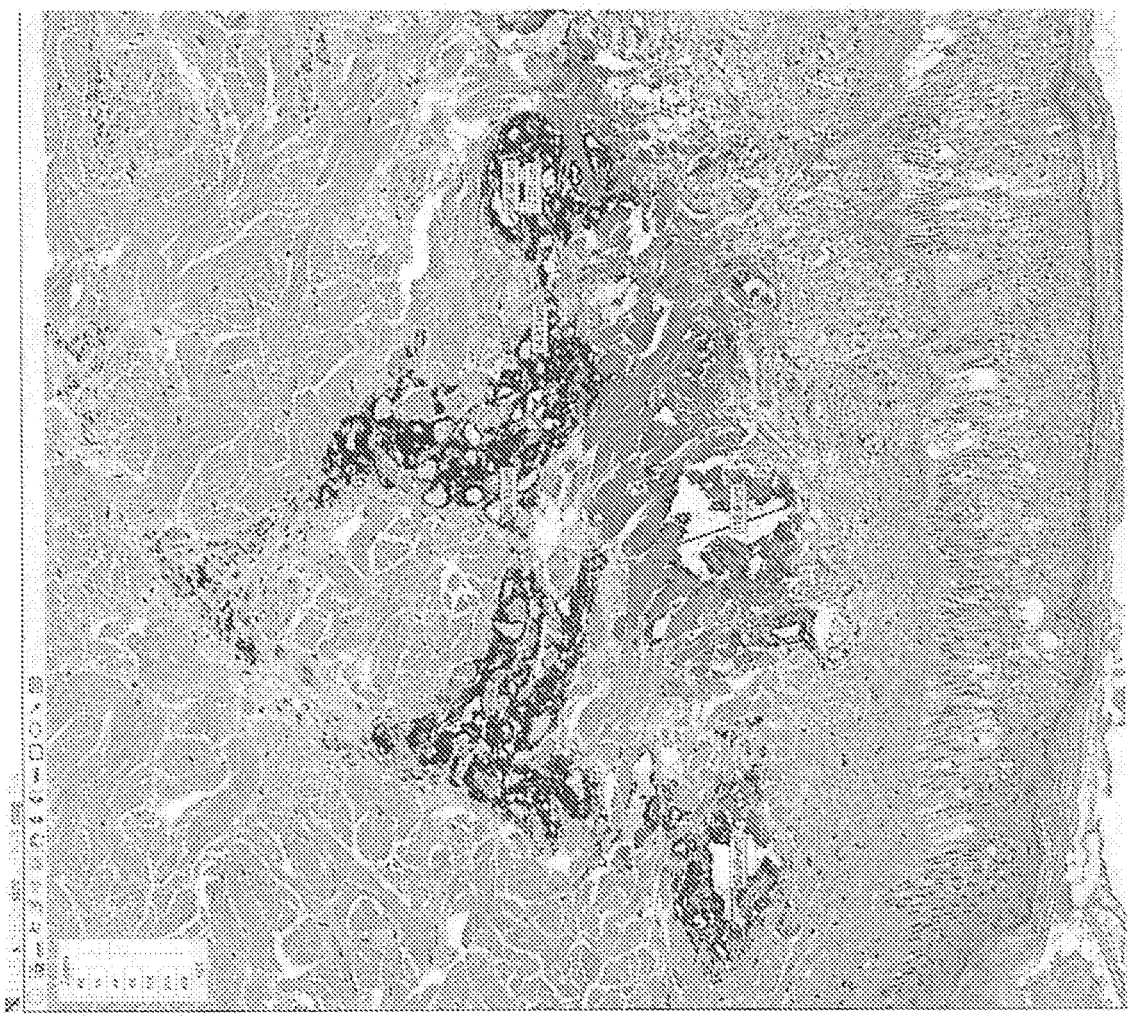
FIG. 19 depicts a histological image of skin illustrating the size of intradermal vacuoles.

As shown in FIG. 19, intradermal vacuoles caused by laser treated skin vary in size from <2 micrometers to >100 micrometers. These intradermal vacuoles are not encapsulated like contrast microbubbles found in the prior art. Unlike the superficial dermal vacuoles which begin to dissipate after 20 minutes, these deep dermal vacuoles are relatively stable. Histological analysis from two (2) hours after laser treatment indicate a significant number of deep vacuoles present around tattoo pigment particle agglomerations. Even after forty eight (48) hours, these deep vacuoles are still present indicating the vacuoles, unlike bubbles, are relatively stable. However, by this time they have filled with fluid or fibrin material. This provides evidence that the vacuoles are not bubbles similar to what had been seen in the prior art.

Given the size of the deep dermal vacuoles, unexpected results were achieved when the pulsed acoustic waves were successfully used to quickly clear these vacuoles, despite their high stability.

D. Method of Treating Additional Maladies and Conditions

In addition to tattoo removal, embodiments of the present methods may include the application of high-frequency shockwaves to supplement and/or assist a variety of laser-based skin treatments that result in the epidermal and intradermal vacuoles previously discussed. Some embodiments of the present systems and methods may be used to assist in any laser procedure that results in the immediate formation of superficial and deep vacuoles. As with the removal of tattoos, the formation of epidermal and intradermal vacuoles limits the ability of repeat effective laser treatment due to the shielding or blocking of subsequent laser pulses by the vacuoles. As a result, repeat laser treatments usually cannot be administered without a long duration rest period.

For example, such additional laser-based treatments that would benefit from embodiments of the present systems and methods may include: laser skin resurfacing, laser removal of birthmarks, laser removal of skin lesions, laser hair transplants, laser scar removal, laser-assisted hair reduction, laser removal of vascular lesions, laser lip lightening, and/or laser treatment of melasma.

Some embodiments where the present method or system may be implemented include systems or method that use lasers to treat pigmented epidermal and/or dermal lesions on a patient. Such treatment may include the use of 532 nm (frequency doubled Nd:YAG) laser or 1064 nm laser and may include the treatment of lentigines, café-au-lait macules, freckles, and/or dermal pigmented lesions.

In other embodiments, the present method and systems may be used during laser skin resurfacing including medium depth nonablative skin resurfacing and/or nonablative skin resurfacing for wrinkles and acne scars. Such an embodiment may use a frequency doubled 532 nm Q switched laser or a Q-switched Nd:YAG 1064 nm laser.

Additional embodiments include implementing the present method and system in laser treatment of melasma. Such an embodiment may comprise the use of a 694 nm Q-switched ruby laser, a 755 nm Q-switched alexandrite laser, a 532 nm frequency doubled Q-switched Nd:YAG laser, and/or a 1064 nm Q-switched Nd:YAG laser. Additional embodiments include implementing the present method and system in laser-assisted hair reduction using a Q-switched laser, laser treatment of vascular lesions using a Medlite™ laser from Hoya ConBio, or laser lip lightening using a Q-switched 532 nm laser.

The above specification and examples provide a description of the structure and use of exemplary embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the present devices are not intended to be limited to the particular forms disclosed. Rather, they include all modifications and alternatives falling within the scope of the claims, and embodiments other than the one shown may include some or all of the features of the depicted embodiment. For example, components may be combined as a unitary structure. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A method for acoustic treatment of tissue to disperse vacuoles within the tissue, the method comprising:
   identifying a location of tissue containing intradermal vacuoles;
   coupling an acoustic wave generator to the tissue containing the intradermal vacuoles; and
   directing pulsed acoustic waves from the acoustic wave generator into the tissue containing the intradermal vacuoles to thereby disperse the intradermal vacuoles;
   wherein the intradermal vacuoles include non-encapsulated vacuoles, the non-encapsulated vacuoles being devoid of tattoo pigment particle agglomerations.

2. The method of claim 1, further comprising treating a section of the tissue with a laser to generate the intradermal vacuoles in the tissue.

3. The method of claim 2, further comprising treating the section of the tissue with the laser after directing pulsed acoustic waves from the acoustic wave generator into the section of the tissue.

4. The method of claim 3 where:
   the section of the tissue includes tattooed skin;
   the method comprises repeated steps of treating the tattooed skin with the laser and subsequently treating the tattooed skin with the acoustic wave generator; and
   the skin is treated with an acoustic wave generator for between about 0.1 minute and about 10 minutes.

5. The method of claim 3, further comprising:
   treating the section of the tissue with a laser after directing pulsed acoustic waves from the acoustic wave generator into the tissue; and
   repeating directing and treating in alternating fashion for at least 2 iterations in a single treatment session.

6. The method of claim 5, where treating the section of the tissue with a laser is performed within 10 minutes of directing the pulsed acoustic waves.

7. The method of claim 1, where:
   the intradermal vacuoles are formed via treatment of the tissue with laser light; or
   the intradermal vacuoles do not include tattoo pigment particle agglomerations.

8. A method of tattoo removal, the method comprising:
   directing laser light to a portion of tissue at a first time to form intradermal vacuoles;
   directing a first plurality of shockwaves to the portion of the tissue to breakup and disperse the intradermal vacuoles; and
   after directing the first plurality of shockwaves, directing laser light to the portion of the tissue at a second time;
   wherein the intradermal vacuoles include non-encapsulated vacuoles, the non-encapsulated vacuoles being devoid of tattoo pigment particle agglomerations.

9. The method of claim 8, further comprising:
   directing a second plurality of shockwaves to the portion of the tissue; and
   after directing the second plurality of shockwaves, directing laser light to the portion of the tissue at a third time;
   where directing the first plurality of shockwaves and directing the second plurality of shockwaves are performed within 10 minutes or less.

10. The method of claim 8, where directing the first or second plurality of shockwaves to the tissue comprises delivering the shockwaves to at least one of the intradermal vacuoles comprising at least one region of heterogeneity until the at least one intradermal vacuole ruptures or disperses.

11. The method of claim 8, where:
    the first and second plurality of shockwaves are delivered to the portion of the tissue for between about 0.5 minutes and about 20 minutes, or
    directing the laser light to the portion of the tissue comprises applying a laser with a pulse duration of between about 1 nanosecond and about 1 microsecond to the portion of the tissue.

12. The method of claim 8, where:
    the first or second plurality of shockwaves include:
        a frequency between about 700 KHz and about 100 Mhz,
        a pulse duration between about 1 nanosecond and about 1 microsecond, or
        a pulse rate between about 10 Hz and about 1 KHz; and
    the intradermal vacuoles do not include tattoo pigment particle agglomerations.

* * * * *